(12) United States Patent
Smith et al.

(10) Patent No.: US 6,537,993 B2
(45) Date of Patent: Mar. 25, 2003

(54) COMPOUNDS FOR ENHANCING CHEMOTHERAPY

(75) Inventors: Charles D. Smith, Hershey, PA (US); David S. Lawrence, Olney, MD (US)

(73) Assignee: Penn State Research Foundation, University Park, PA (US)

( * ) Notice: Subject to any disclaimer, the term of this patent is extended or adjusted under 35 U.S.C. 154(b) by 0 days.

(21) Appl. No.: 09/822,743

(22) Filed: Mar. 30, 2001

(65) Prior Publication Data

US 2002/0013322 A1 Jan. 31, 2002

Related U.S. Application Data

(60) Provisional application No. 60/193,109, filed on Mar. 30, 2000, and provisional application No. 60/193,104, filed on Mar. 30, 2000.

(51) Int. Cl.⁷ .................... A61K 31/498; A61K 31/437; C07D 241/44; C07D 471/04
(52) U.S. Cl. .................. 514/249; 514/292; 546/84; 544/354
(58) Field of Search ............................ 544/354; 514/249

(56) References Cited

FOREIGN PATENT DOCUMENTS

| | | |
|---|---|---|
| EP | 0430 485 A | 6/1991 |
| WO | WO 01/66143 A | 9/2001 |

OTHER PUBLICATIONS

Lawrence et al. J.Med.Chem. 44(4),pp.594–601 (Dec. 22, 2000).*
Badr et al. Bull.Chem.Soc.Jpn. vol.56, pp.326–330 (1983).*
Chemical Abstracts, vol. 99, No. 3, 1983, Columbus, Ohio, US; abstract No. 16559u, p. 75; col. 1; XP002177807.
Smith, Leon et al., "A Novel and Highly efficient synthesis of the aza analogs of tacrine" Tetrahedron Lett. (1999), 40(31), 5643–5646.
Database CA Online! Chemical Abstracts Service, Columbus, Ohio, US; Kiyoi, Takao et al., "Prepareation and formulation of furoylpiperazine derivatives as selectin inhibitors" XP002184104.
Leach, Colin A. et al., J. Med. Chem. (1992), 35(10), 1845–52, XP002184101.
Toth, Gabor et al., Liebigs Ann. Chem. (1991), (11), 1215–19, XP002184102.
Database CA Online! Chemical Abstracts Service, Fujimura, Hajime et al. XP002184105.
Database CA Online! Chemical Abstracts Service, Fujimura, Hajime et al., XP002184106.
Richter, Reinhard et al., J. Org. Chem. (1973), 38(15), 2614–7, XP002184103.
Database CA Online, Taruie Naoki et al., XP002184107.
Gottesman and Pastan, 1993, Ann. Rev. Biochem. 62:385–427.
Cole et al., 1994, Cancer Res. 54:5902–10.
Smith et al., 1995, Cancer 75:2597–604.
Leveille–Webster and Areas 1995, J. Membrane Bol. 143:89–102.
Zaman et al., 1993, Cancer Res. 53:1747.
Goldstein et al., 1989, J. Natl. Cancer Inst. 81:116–124.
Abbaszadegan et al., 1994 Cancer Res. 54:4676–79.
Thomas et al., 1994, Eur. J. Cancer 30A:1705–09.
Schinkel et al., 1996, J. Clin Invest. 97:2517–24.
Holash and Stewart, 1993, Brain Res. 629:218–24.
Holash et al., 1993, Proc. Natl. Acad. Sci. U.S.A. 90:11069–73.
Lum and Gosland, 1995, Hematol Oncol. Clin. North Amer. 9:319–36.
Sparreboom et al., 1997 Proc. Natl. Acad. Sci. USA 94:2031–35.
Gupta and Gollupudi 1993 J. Clin. Immunol. 13:289–301.
Yusa et al 1990 Biochem Biophys Res. Com 169:986–90.
Salmon & Dalton 1996 J. Rhumatol Suppl 44:97–101.
Ulman, 1995 J. Bioenergetics Biomembranes 27:77–84.
Frappeir et al., 1996 Antimicrob Agents Chemoth 40:1476–81.

* cited by examiner

*Primary Examiner*—Emily Bernhardt
(74) *Attorney, Agent, or Firm*—McDonnell Boehnen Hulbert & Berghoff

(57) ABSTRACT

The present invention provides 1H-quinoxalinones, of the formula:

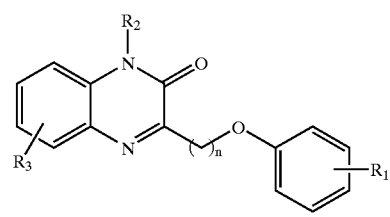

or pharmaceutically acceptable salts thereof, wherein $R_1$, $R_2$, $R_3$, and n are as defined herein. Also disclosed are pharmaceutical compositions comprising such compounds, and methods for using the compounds to increase the therapeutic efficacy of drugs.

13 Claims, 7 Drawing Sheets

COMPOUNDS FOR ENHANCING CHEMOTHERAPY

This application claims the benefit of U.S. Provisional Patent Application No. 60/193,109, filed on Mar. 30, 2000, and No. 60/193,104, filed on Mar. 30, 2000, the disclosure of each of which is explicitly incorporated by reference herein.

This invention was made with government support Grant CA64983 awarded by the United States Public Health Service. The government has certain rights in the invention.

BACKGROUND OF THE INVENTION

1. Field of the Invention

This invention relates to chemical compounds, pharmaceutical compositions, and methods for increasing the therapeutic efficacy of drugs. Specifically, the invention relates to compounds and pharmaceutical compositions for inhibiting drug transport proteins that efflux therapeutic agents from cells, and to methods for using these compounds and compositions to increase the efficacy of the therapeutic agents that are effluxed by these drug transport proteins.

2. Background of the Invention

Eukaryotic cells possess integral membrane transport proteins which actively efflux a variety of chemical compounds from the cells (Gottesman and Pastan, 1993, *Ann. Rev. Biochem.* 62:385–427). In normal cells, these transport proteins serve to protect cells from cytotoxic and mutagenic compounds encountered in the diet or environment. However, these transport proteins are also very effective at removing pharmaceutical agents from target cells, thereby severely restricting the therapeutic efficacy of such agents. Consequently, compounds that inhibit these transport proteins are expected to enhance the clinical utility of drugs susceptible to such transport by enhancing drug accumulation in target cells.

Two transport proteins, P-glycoprotein (P-gp) and multidrug resistance-associated protein (MRP), play important roles in the treatment of human disease. Because of this involvement in human disease, there is great interest in developing pharmaceutical agents that will effectively inhibit the function of these proteins. More recently, additional transport proteins have been identified, including cMOAT and some proteins related to MRP.

An important issue regarding P-gp and MRP relates to their substrate specificity. Pharmacological comparisons of cells overexpressing either P-gp or MRP demonstrate only a partial overlap of the resistance profiles conferred by these two proteins. For example, while MRP-transfected cells show a greater resistance to vincristine, etoposide, and doxorubicin, than to vinblastine and paclitaxel (Cole et al., 1994, *Cancer Res.* 54:5902–10), P-gp-transfected cells show a much greater resistance to vinblastine and paclitaxel (Smith et al., 1995, *Cancer* 75:2597–604). This differential pharmacology illustrates the feasibility of developing selective inhibitors of these transporters, which should provide useful methods for increasing the therapeutic efficacy of many types of pharmaceutical agents.

Another significant difference between P-gp and MRP relates to the distribution of these proteins in normal tissues. P-gp has been shown to be expressed by several types of secretory cells, such as capillary endothelial cells in the brain and testis, and at sites within the pancreas, kidney, and liver (Leveille-Webster and Arias, 1995, *J. Membrane Biol.* 143:89–102). In contrast, the expression of MRP mRNA occurs in virtually every type of tissue (Zaman et al., 1993, *Cancer Res.* 53:1747). Cells in various disease states also differentially express P-gp and MRP, indicating that selective inhibitors will be preferred as therapeutic agents.

An example of transport protein-mediated drug resistance is the phenomenon of multidrug resistance (MDR), which is often encountered in cancer chemotherapy (Gottesman and Pastan, 1993). As a result of this phenomenon, tumor cells expressing transport proteins become resistant to many structurally unrelated drugs and the proliferation of resistant tumor cells results in the failure of chemotherapeutic treatment. Tumor cells from individuals undergoing chemotherapy often demonstrate elevated P-gp expression (Goldstein et al., 1989, *J. Natl. Cancer Inst.* 81:116–24). Recent studies have also indicated that MRP is expressed in a high percentage of solid tumors and leukemias. However, no differences in MRP levels were detected between normal and malignant hematopoietic cells (Abbaszadegan et al., 1994, *Cancer Res.* 54:4676–79), and MRP levels were found to be lower in some tumors than in corresponding normal tissues (Thomas et al., 1994, *Eur. J. Cancer* 30A:1705–09). Therefore, it appears that different tumors display different patterns of expression of P-gp and MRP (and perhaps other transport proteins as well).

Another example of drug transporter-mediated resistance is encountered in the effort to deliver drugs to the central nervous system, testes, and eye. In the brain, the blood-brain barrier exists to exclude toxic agents from the brain, and largely derives from the high level of expression of P-gp by endothelial cells in the capillaries of the brain (Schinkel et al., 1996, *J. Clin. Invest.* 97:2517–24). P-gp is also highly expressed in the capillary endothelial cells of the eye (Holash and Stewart, 1993, *Brain Res.* 629:218–24) and testes (Holash et al., 1993, *Proc. Natl. Acad. Sci. U.S.A.* 90:11069–73), restricting the uptake of many compounds by these tissues. While these systems are useful in protecting normal tissues, they also impair the delivery of therapeutic agents to these sites when such delivery may be desired. For example, the expression of P-gp in brain capillary cells impairs effective treatment of brain tumors or neurological diseases using drugs that are transported by P-gp. P-gp is also highly expressed in the liver, adrenal gland, and kidney (Lum and Gosland, 1995, *Hematol Oncol. Clin. North Amer.* 9:319–36), other tissues in which drug delivery is restricted. It is envisioned that inhibition of P-gp, or other transport proteins, will facilitate drug delivery to these sites and so enhance the effectiveness of chemotherapy. It is also envisioned that drug transport protein antagonists will be useful in suppressing the secretion of endogenous compounds, including steroid hormones and cholesterol, providing therapeutic benefit under conditions in which excessive circulating levels of these compounds promote disease states.

Another example of drug transporter-mediated resistance is encountered in the effort to orally deliver therapeutic agents. The high expression of P-gp at the brush-border membrane of the small intestine reduces the bioavailability of orally administered drugs subject to transport (Sparreboom et al., 1997, *Proc. Natl. Acad. Sci. U.S.A.* 94:2031–35). It is envisioned that inhibition of P-gp, or other transport proteins, will facilitate drug absorption, thereby enhancing the effectiveness of chemotherapy.

Yet another example of drug transporter-mediated resistance is encountered in the effort to deliver therapeutic agents to certain leukocytes. P-gp is highly expressed by certain subtypes of lymphocytes, natural killer cells, and bone marrow stem cells (Gupta and Gollapudi, 1993, *J. Clin. Immunol.* 13:289–301). This reduces the therapeutic efficacy of drugs targeting these cells, including anti-HIV compounds for the treatment of AIDS (Yusa et al., 1990, *Biochem. Biophys. Res. Com.* 169:986–90). Furthermore, the release of inflammatory cytokines and other immunomodulators appears to involve drug transporters (Salmon and Dalton, 1996, *J. Rheumatol. Suppl.* 44:97–101). It is envisioned that inhibition of P-gp, or other transport proteins, will facilitate drug accumulation in these cells and so enhance the effectiveness of chemotherapy.

Organisms other than mammals also possess transport proteins similar to P-gp that have been shown to confer resistance to chemotherapeutic agents (Ullman, 1995, *J. Bioenergetics Biomembranes* 27:77–84). While the pharmacology of these transport proteins is not identical to that of P-gp, certain modulators are able to inhibit drug transport by both P-gp and for example, protozoan transport proteins (Frappier et al., 1996, *Antimicrob. Agents Chemother.* 40:1476–81). It is envisioned that certain MDR modulators will facilitate drug accumulation in non-mammalian cells and so enhance the effectiveness of anti-infection chemotherapy.

Since drug transport proteins are involved in determining the success of chemotherapy in a variety of disease states, there is a need for effective modulators of drug transport proteins. While a number of compounds have been shown to reverse transporter-mediated MDR in cell culture, the clinical success of these modulators has been unimpressive, predominantly due to their intrinsic toxicity and undesired effects on the pharmacokinetics of accompanying drugs. However, the failure of these modulators can also be attributed to their lack of selectivity for different drug transport proteins. For example, inhibition of MRP by MDR modulators is likely to increase the uptake of cytotoxic anticancer drugs by many normal tissues, thereby resulting in greater toxicity in the individual. Successful chemotherapy will consequently require a panel of transporter antagonists with differential selectivity for P-gp and MRP that will allow selection of the appropriate sensitizing agent. Thus, there remains a need in the art to develop drug transport protein modulators that are selective for P-gp and MRP. The development of such modulators, and methods for their use, would have wide application in the medical art.

SUMMARY OF THE INVENTION

The present invention provides chemical compounds, pharmaceutical compositions, and methods for increasing the therapeutic efficacy of drugs. Specifically, the invention provides compounds and pharmaceutical compositions for inhibiting drug transport proteins that efflux therapeutic agents from cells, and to methods for using these compounds and compositions to increase the efficacy of the therapeutic agents that are effluxed by these drug transport proteins.

The present invention provides chemical compounds of the formula:

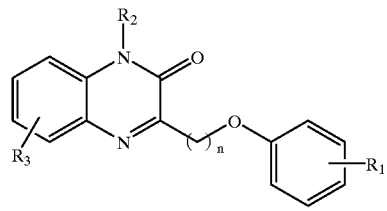

wherein
n is an integer from 1 to 12, preferably n is 1;
$R_1$ is H, alkyl ($C_1$–$C_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl ($C_1$–$C_6$);

$R_2$ is H, alkyl ($C_1$–$C_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl ($C_1$–$C_6$);

$R_3$ is H, alkyl ($C_1$–$C_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl ($C_1$–$C_6$); and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein each of the above is optionally substituted with up to 5 groups that are independently alkyl ($C_1$–$C_6$), alkoxy ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl ($C_1$–$C_6$); or pharmaceutically acceptable salts thereof.

The present invention also provides chemical compounds of the formula:

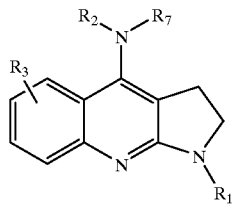

or a pharmaceutically acceptable salt thereof wherein, $R_1$ is H, alkyl ($C_1$–$C_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, arylalkanoyl, —COOH, carboxamide, mono or dialkylaminocarboxamide, —SH, —S-alkyl, —$CF_3$, —$OCF_3$, —$NO_2$, —$NH_2$, —$CO_2R_8$, —$OC(O)R_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, —$CO_2H$, —SH, —S-alkyl, —$NO_2$, or —NR'R", wherein R' and R" are independently H or alkyl ($C_1$–$C_6$);

$R_2$ is H, alkyl ($C_1$–$C_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, —COOH, carboxamide, mono or dialkylaminocarboxamide, —SH, —S-alkyl, —$CF_3$, —$OCF_3$, —$NO_2$, —$NH_2$, —$CO_2R_8$, —$OC(O)R_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, —$CO_2H$, —SH, —S-alkyl, —$NO_2$, or —NR'R", wherein R' and R" are independently H or alkyl ($C_1$–$C_6$); or $R_2$ is:

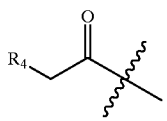

wherein $R_4$ represents H, alkyl ($C_1$–$C_6$), halogen, haloalkyl, —OH, alkoxy, hydroxyalkyl, —SH, —S-alkyl, —$NO_2$, —$NH_2$, mono- or dialkylamino, aminoalkyl, mono- or dialkylaminoalkyl, heterocycloalkyl, preferably pyrrolyl, morpholinyl, thiomorpholinyl, piperidyl, or piperazyl, heterocycloalkylalkyl, aryl, preferably phenyl, or arylalkyl, preferably benzyl, heteroaryl, or heteroarylalkyl;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, —$CO_2H$, —SH, —S-alkyl, —$NO_2$, or —NR'R", wherein R' and R" are independently H or alkyl ($C_1$–$C_6$);

$R_3$ is H, alkyl ($C_1$–$C_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, —COOH, carboxamide, mono or dialkylaminocarboxamide, —SH, —S-alkyl, —$CF_3$, —$OCF_3$, —$NO_2$, —$NH_2$, —$CO_2R_8$, —$OC(O)R_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, —$CO_2H$, —SH, —S-alkyl, —$NO_2$, or —NR'R", wherein R' and R" are independently H or alkyl ($C_1$–$C_6$);

$R_7$ is H, alkyl ($C_1$–$C_6$), alkoxy, alkoxycarbonyl, preferably tertiary-butoxycarbonyl (BOC), arylalkyl, preferably benzyl, or arylalkoxycarbonyl, preferably carbobenzyloxy (Cbz), wherein each is optionally substituted with up to three groups that are independently alkyl, alkoxy, —$NO_2$, —OH, halogen, —CN, —$CF_3$, or —$OCF_3$; and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein each of the above is optionally substituted with up to 5 groups that are independently alkyl ($C_1$–$C_6$), alkoxy ($C_1$–$C_6$), halogen, haloalkyl, —$CF_3$, —$OCF_3$, —OH, alkoxy, hydroxyalkyl, —CN, —$CO_2H$, —SH, —S-alkyl, —$NO_2$, or —NR'R", wherein R' and R" are independently H or alkyl ($C_1$–$C_6$).

The present invention provides pharmaceutical compositions comprising a compound of the formula:

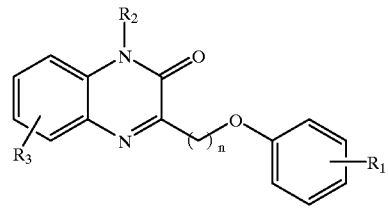

or a pharmaceutically acceptable salt thereof; with at least one pharmaceutically acceptable carrier or excipient, wherein n is an integer from 1 to 12, preferably n is 1;

$R_1$ is H, alkyl ($C_1$–$C_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —$CF_3$, —$OCF_3$, —$NO_2$, —$NH_2$, —$CO_2R_8$, —$OC(O)R_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$);

R$_2$ is H, alkyl (C$_1$–C$_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$);

R$_3$ is H, alkyl (C$_1$–C$_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$); and R$_8$ is H, alkyl, aryl, arylalkyl, cycloalkyl, cycloalkylalkyl, heteroaryl, heteroarylalkyl, heterocycloalkyl, or heterocycloalkylalkyl;

wherein each of the above is optionally substituted with up to 5 groups that are independently alkyl (C$_1$–C$_6$), alkoxy (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$).

The present invention also provides pharmaceutical compositions comprising a compound of the formula:

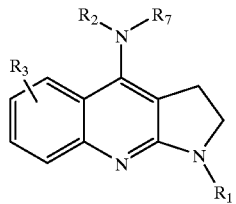

or a pharmaceutically acceptable salt thereof; with at least one pharmaceutically acceptable carrier or excipient wherein, R$_1$ is H, alkyl (C$_1$–C$_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, alkanoyl, arylalkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$);

R$_2$ is H, alkyl (C$_1$–C$_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$); or R$_2$ is:

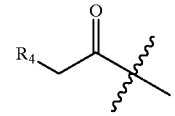

wherein R$_4$ represents H, alkyl (C$_1$–C$_6$), halogen, haloalkyl, —OH, alkoxy, hydroxyalkyl, —SH, —S-alkyl, —NO$_2$, —NH$_2$, mono- or dialkylamino, aminoalkyl, mono- or dialkylaminoalkyl, heterocycloalkyl, preferably pyrrolyl, morpholinyl, thiomorpholinyl, piperidyl, or piperazyl, heterocycloalkylalkyl, aryl, preferably phenyl, or arylalkyl, preferably benzyl, heteroaryl, or heteroarylalkyl;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$);

R$_3$ is H, alkyl (C$_1$–C$_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$);

R$_7$ is H, alkyl (C$_1$–C$_6$), alkoxy, alkoxycarbonyl, preferably tertiary-butoxycarbonyl (BOC), arylalkyl, preferably benzyl, or arylalkoxycarbonyl, preferably carbobenzyloxy (Cbz), wherein each is optionally substituted with up to three groups that are independently alkyl, alkoxy, —NO$_2$, —OH, halogen, —CN, —CF$_3$, or —OCF$_3$; and R$_8$ is H, alkyl, aryl, arylalkyl, cycloalkyl, cycloalkylalkyl, heteroaryl, heteroarylalkyl, heterocycloalkyl, or heterocycloalkylalkyl;

wherein each of the above is optionally substituted with up to 5 groups that are independently alkyl (C$_1$–C$_6$), alkoxy (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$).

The present invention provides methods for inhibiting drug transport from target cells or tissues in an animal undergoing chemotherapy, comprising administering to the animal a pharmaceutical composition of the present invention in an amount effective to inhibit drug transport from the target cells or tissues of the animal. The present invention also provides methods for preventing drug resistance in an animal undergoing chemotherapy, comprising administering to the animal a pharmaceutical composition of the present invention in an amount effective to attenuate drug resistance. The methods of the present invention may be useful for treating MDR—by reversing MDR or chemosensitizing multidrug resistant cells to anti-cancer agents—or preventing MDR.

The present invention further provides methods for enhancing the therapeutic efficacy of an antiproliferative drug in target cells or tissues of an animal, comprising administering to the animal a pharmaceutical composition of the present invention in an amount effective to enhance delivery of the antiproliferative drug to the target cells or tissues of the animal.

The present invention still further provides methods for enhancing the therapeutic efficacy of an anti-infective agent in an animal, comprising administering to the animal a pharmaceutical composition of the present invention in an amount effective to inhibit drug transport from an infectious agent in the animal.

The present invention still further provides methods for enhancing the delivery of a therapeutic agent to target cells or tissues of an animal, comprising administering to the animal a pharmaceutical composition of the present invention in an amount effective to enhance delivery of the therapeutic agent to the target cells or tissues of the animal. The methods of the present invention may be useful for enhancing the delivery to target cells or tissues such as the brain, testes, eye, or leukocytes.

The present invention still further provides methods for enhancing the absorption of an orally-delivered therapeutic agent in an animal, comprising administering to the animal a pharmaceutical composition of the present invention in an amount effective to enhance drug transport across the gastrointestinal tract.

The present invention provides a panel of novel drug transport inhibitors. The chemical compounds, pharmaceutical compositions, and methods of the present invention provide important new therapeutic tools for treating or preventing a variety of diseases or conditions related to drug transport.

Specific preferred embodiments of the present invention will become evident from the following more detailed description of certain preferred embodiments and the claims.

DETAILED DESCRIPTION OF THE PREFERRED EMBODIMENTS

Figure 1:
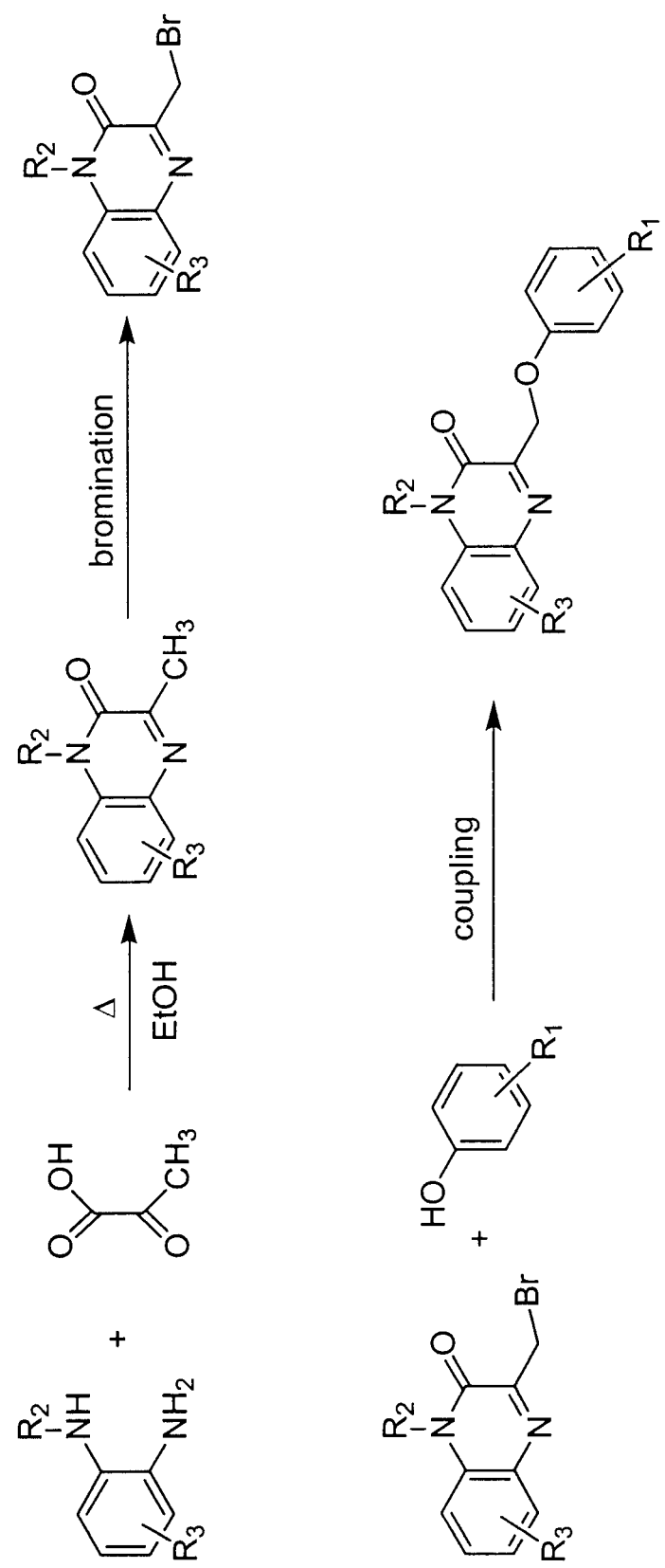
FIG. 1 illustrates one scheme for the synthesis of the phenoxymethylquinoxalinone compounds of the present invention.

The present invention provides chemical compounds, pharmaceutical compositions, and methods for increasing the therapeutic efficacy of drugs. The chemical compounds and pharmaceutical compositions of the present invention may be useful in preventing drug resistance or inhibiting drug transport in an animal undergoing chemotherapy, enhancing the therapeutic efficacy of an antiproliferative drug or an anti-infective agent in an animal, enhancing the delivery of a therapeutic agent in an animal, or enhancing the absorption of an orally-delivered therapeutic agent in an animal.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

The term "alkyl" includes those alkyl groups of a designed number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkyl" refers to a C$_3$–C$_8$ cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C$_3$–C$_7$ cycloalkyl group attached to the parent molecular moiety through an alkyl group, as defined above. Examples of cycloalkylalkyl groups include cyclopropylmethyl and cyclopentylethyl.

The terms "halogen" or "halo" indicate fluorine, chlorine, bromine, or iodine.

The term "heterocycloalkyl," refers to a non-aromatic ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

In certain situations, the compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

In one embodiment, the chemical compound of the present invention is a compound of the formula:

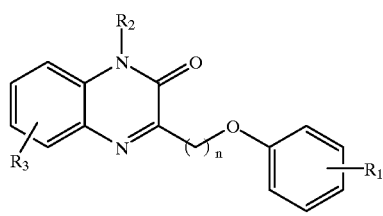

(I)

or a pharmaceutically acceptable salt thereof wherein, n is an integer from 1 to 12, preferably n is 1;

$R_1$ is H, alkyl ($C_1$–$C_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, amino alkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R'and R" are independently H or alkyl ($C_1$–$C_6$);

$R_2$ is H, alkyl ($C_1$–$C_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl ($C_1$–$C_6$);

$R_3$ is H, alkyl ($C_1$–$C_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl ($C_1$–$C_6$); and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein each of the above is optionally substituted with up to 5 groups that are independently alkyl ($C_1$–$C_6$), alkoxy ($C_1$–$C_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl ($C_1$–$C_6$).

Non-toxic pharmaceutically acceptable salts of the compounds of the present invention include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of the present invention.

The invention also encompasses the acylated prodrugs of the compounds of the present invention. Those skilled in the art will recognize various synthetic methodologies, which may be employed to prepare non-toxic pharmaceutically acceptable addition salts and acylated prodrugs of the compounds encompassed by the present invention.

In a more preferred embodiment, compound (I) is defined such that:

n is an integer from 1 to 6;

$R_1$, and $R_3$ are independently H, alkyl ($C_1$–$C_{15}$), cycloalkyl, cycloalkylalkyl, aryl, preferably phenyl, arylalkyl, preferably benzyl, halogen, haloalkyl, —OH, alkoxy, hydroxyalkyl, alkanoyl, carboxamide, mono or dialkylaminocarboxamide, —CF$_3$, —OCF$_3$, —NO$_2$, —NH$_2$, —CO$_2$R$_8$, —OC(O)R$_8$, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, or —NR'R", wherein R' and R" are independently H or alkyl ($C_1$–$C_6$);

$R_2$ is H, alkyl ($C_1$–$C_8$), cycloalkyl, cycloalkylalkyl, aryl, preferably phenyl, arylalkyl, preferably benzyl, halogen, haloalkyl, —OH, alkoxy, hydroxyalkyl, alkanoyl, carboxamide, mono or dialkylaminocarboxamide, —CO$_2$R$_8$, —OC(O)R$_8$, carbamoyl, mono or dialkylcarbamoyl, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, or —NR'R", wherein R' and R" are independently H or alkyl ($C_1$–$C_6$); and $R_8$ is H, alkyl, aryl, arylalkyl, cycloalkyl, or cycloalkylalkyl;

wherein each of the above is optionally substituted with up to 5 groups that are independently alkyl ($C_1$–$C_6$), alkoxy ($C_1$–$C_6$), halogen, —CF$_3$, —OCF$_3$, —OH, hydroxyalkyl, —CN, —CO$_2$H, or —NR'R", wherein R' and R" are independently H or alkyl ($C_1$–$C_6$).

In another preferred embodiment, compound (I) is defined such that:

n is 1;

$R_1$ is H, alkyl ($C_1$–$C_{15}$), cycloalkyl, cycloalkylalkyl, aryl, preferably phenyl, arylalkyl, preferably benzyl, halogen, haloalkyl, —OH, alkoxy, hydroxyalkyl, alkanoyl, carboxamide, mono or dialkylaminocarboxamide, —CF$_3$, —OCF$_3$, —NO$_2$, —NH$_2$, —CO$_2$R$_8$, —OC(O)R$_8$, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, or —NR'R", wherein R' and R" are independently H or alkyl ($C_1$–$C_6$);

$R_2$ is H, alkyl ($C_1$–$C_8$), cycloalkyl, cycloalkylalkyl, aryl, preferably phenyl, arylalkyl, preferably benzyl, halogen, haloalkyl, —OH, alkoxy, hydroxyalkyl, alkanoyl, carboxamide, mono or dialkylaminocarboxamide, —CO$_2$R$_8$, —OC(O)R$_8$, carbamoyl, mono or dialkylcarbamoyl, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, or —NR'R", wherein R' and R" are independently H or alkyl ($C_1$–$C_6$);

$R_3$ is H, alkyl ($C_1$–$C_6$), alkoxy, halogen, alkanoyl, —CF$_3$, or —OCF$_3$; and $R_8$ is alkyl, aryl, arylalkyl, cycloalkyl, or cycloalkylalkyl;

wherein each of the above is optionally substituted with up to 5 groups that are independently alkyl ($C_1$–$C_6$), alkoxy ($C_1$–$C_6$), halogen, —CF$_3$, —OCF$_3$, —OH, hydroxyalkyl, —CN, —CO$_2$H, or —NR'R", wherein R' and R" are independently H or alkyl ($C_1$–$C_6$).

Preferred embodiments of the phenoxymethylquinoxalinone compounds of the present invention include 1,3-Dimethyl-1H-quinoxalin-2-one; 1-Methyl-3-phenoxymethyl-1H-quinoxalin-2-one; 3-(4-Cyano-phenoxymethyl)-1-methyl-1H-quinoxalin-2-one; 3-(3-tert-Butyl-phenoxymethyl)-1-methyl-1H-quinoxalin-2-one; 3-(4-Benzoyl-phenoxymethyl)-1-methyl-1H-quinoxalin-2-one; 3-Methoxy-4-(4-methyl-3-oxo-3,4-dihydroquinoxalin-2-yl-methoxy)-benzoyl methyl ester; 2-(4-Methyl-3-oxo-3,4-dihydroquinoxalin-2-yl-methoxy)-N-phenylbenzamide; 4-(4-Methyl-3-oxo-3,4-dihydro-quinoxalin-2-ylmethoxy)-benzoyl ethyl ester; 2-(4-Benzyl-3-oxo-3,4-dihydroquinoxalin-2-ylmethoxy)-N-phenylbenzamide; or pharmaceutically acceptable salts thereof.

Particularly preferred embodiments of the phenoxymethylquinoxalinone compounds of the present invention include 2-(4-Methyl-3-oxo-3,4-dihydroquinoxalin-2-yl-methoxy)-N-phenylbenzamide and 2-(4-Benzyl-3-oxo-3,4-dihydroquinoxalin-2-ylmethoxy)-N-phenyl-benzamide.

The phenoxymethylquinoxalinone compounds of the present invention may be synthesized according to reaction scheme shown in FIG. 1. The reactions as shown in FIG. 1 will occur with a wide variety of $R_1$-substituted phenols and virtually any $R_2$- and $R_3$-substituted diaminobenzene compound, allowing the rapid synthesis of very diverse families of phenoxymethyiquinoxalinone compounds. A large number of starting materials are available from Aldrich Chemical Company and other chemical suppliers.

In another embodiment, the chemical compound of the present invention is a pyrroloquinoline of the formula:

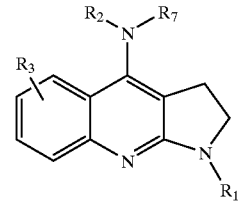

or a pharmaceutically acceptable salt thereof, wherein
$R_1$ is H, alkyl ($C_1$–$C_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, alkanoyl, arylalkanoyl, —COOH, carboxamide, mono or dialkylaminocarboxamide, —SH, —S-alkyl, —CF$_3$, —OCF₃, —NO₂, —NH₂, —CO₂R₈, —OC(O)R₈, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C₁–C₆), halogen, haloalkyl, —CF₃, —OCF₃, —OH, alkoxy, hydroxyalkyl, —CN, —CO₂H, —SH, —S-alkyl, —NO₂, or —NR'R", wherein R' and R" are independently H or alkyl (C₁–C₆);

R₂ is H, alkyl (C₁–C₁₅), cycloalkyl, cycloalkylalkyl, aryl, arylalkyl, heteroaryl, heteroarylalkyl, heterocycloalkyl, heterocycloalkylalkyl, haloalkyl, —OH, alkoxy, hydroxyalkyl, —COOH, carboxamide, mono or dialkylaminocarboxamide, —NH₂, —CO₂R₈, —OC(O)R₈, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C₁–C₆), halogen, haloalkyl, —CF₃, —OCF₃, —OH, alkoxy, hydroxyalkyl, —CN, —CO₂H, —SH, —S-alkyl, —NO₂, or —NR'R", wherein R' and R" are independently H or alkyl (C₁–C₆); or R₂ is:

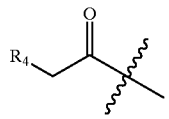

wherein R₄ represents H, alkyl (C₁–C₆), halogen, haloalkyl, —OH, alkoxy, hydroxyalkyl, —SH, —S-alkyl, —NO₂, —NH₂, mono- or dialkylamino, aminoalkyl, mono- or dialkylaminoalkyl, heterocycloalkyl, preferably pyrrolyl, morpholinyl, thiomorpholinyl, piperidyl, or piperazyl, heterocycloalkylalkyl, aryl, preferably phenyl, or arylalkyl, preferably benzyl, heteroaryl, or heteroarylalkyl;

wherein each of the above is optionally substituted with up to 5 groups that are independently alkyl (C₁–C₆), halogen, haloalkyl, —CF₃, —OCF₃, —OH, alkoxy, hydroxyalkyl, —CN, —CO₂H, —SH, —S-alkyl, —NO₂, or —NR'R", wherein R' and R" are independently H or alkyl (C₁–C₆);

R₃ is H, alkyl (C₁–C₁₅), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, —COOH, carboxamide, mono or dialkylaminocarboxamide, —SH, —S-alkyl, —CF₃, —OCF₃, —NO₂, —NH₂, —CO₂R₈, —OC(O)R₈, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C₁–C₆), halogen, haloalkyl, —CF₃, —OCF₃, —OH, alkoxy, hydroxyalkyl, —CN, —CO₂H, —SH, —S-alkyl, —NO₂, or —NR'R", wherein R' and R" are independently H or alkyl (C₁–C₆);

R₇ is H, alkyl (C₁–C₆), alkoxy, alkoxycarbonyl, preferably tertiary-butoxycarbonyl (BOC), arylalkyl, preferably benzyl, or arylalkoxycarbonyl, preferably carbobenzyloxy (Cbz), wherein each is optionally substituted with up to three groups that are independently alkyl, alkoxy, —NO₂, —OH, halogen, —CN, —CF₃, or —OCF₃; and R₈ is H, alkyl, aryl, arylalkyl, cycloalkyl, cycloalkylalkyl, heteroaryl, heteroarylalkyl, heterocycloalkyl, or heterocycloalkylalkyl;

wherein each of the above is optionally substituted with up to 5 groups that are independently alkyl (C₁–C₆), alkoxy (C₁–C₆), halogen, haloalkyl, —CF₃, —OCF₃, —OH, alkoxy, hydroxyalkyl, —CN, —CO₂H, —SH, —S-alkyl, —NO₂, or —NR'R", wherein R' and R" are independently H or alkyl (C₁–C₆).

In a preferred embodiment, the pyrroloquinoline compound of the present invention is of the formula:

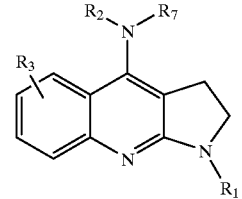

or a pharmaceutically acceptable salt thereof, wherein
R₁ is H, alkyl (C₁–C₆), alkoxy, cycloalkyl, cycolalkylalkyl, alkanoyl, benzyl, or benzoyl;

wherein each of the above is optionally substituted with up to 5 groups that are independently alkyl (C₁–C₆), halogen, haloalkyl, —OH, alkoxy, hydroxyalkyl, —SH, —S-alkyl, —NO₂, or —NR'R", wherein R' and R" are independently H or alkyl (C₁–C₆);

R₂ is H, alkyl (C₁–C₆), cycloalkyl, cycolalkylalkyl, arylalkyl, halogen, haloalkyl, —OH, alkoxy, hydroxyalkyl, carboxamide, mono or dialkylcarboxamido, aminoalkyl, mono- or dialkylaminoalkyl, phenyl, or benzyl;

wherein each of the above is optionally substituted with up to 5 groups that are independently alkyl (C₁–C₆), halogen, haloalkyl, —OH, alkoxy, hydroxyalkyl, —SH, —S-alkyl, —NO₂, or —NR'R", wherein R' and R" are independently H or alkyl (C₁–C₆); or R₂ is:

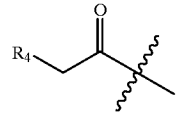

wherein
R₄ represents H, alkyl (C₁–C₆), halogen, haloalkyl, —OH, alkoxy, hydroxyalkyl, —SH, —S-alkyl, —NO₂, —NH₂, mono- or dialkylamino, aminoalkyl, mono- or dialkylamino, pyrrolyl, piperidyl, piperazyl, phenyl, or benzyl;

wherein each of the above is optionally substituted with up to 4 groups that are independently alkyl (C₁–C₆), halogen, haloalkyl, —OH, alkoxy, hydroxyalkyl, —SH, —S-alkyl, —NO₂, or —NR'R", wherein R' and R" are independently H or alkyl (C₁–C₆);

R₃ is H, alkyl (C₁–C₁₅), cycloalkyl, cycolalkylalkyl, halogen, haloalkyl, —OH, alkoxy, hydroxyalkyl, carboxamide, mono or dialkylcarboxamide, —CO$_2$R$_8$, —CF$_3$, —OCF$_3$, —NO$_2$, —NH$_2$, aminoalkyl, mono- or dialkylaminoalkyl, phenyl, or benzyl;

wherein each of the above is optionally substituted with up to 5 groups that are independently alkyl (C$_1$–C$_6$), halogen, haloalkyl, —OH, alkoxy, hydroxyalkyl, —SH, —S-alkyl, —NO$_2$, or —NR'R", wherein R' and R" are H or alkyl (C$_1$–C$_6$);

R$_7$ is H, alkyl (C$_1$–C$_6$), alkoxy, alkoxycarbonyl, preferably tertiary-butoxycarbonyl (BOC), arylalkyl, preferably benzyl, or arylalkoxycarbonyl, preferably carbobenzyloxy (Cbz), wherein each is optionally substituted with up to three groups that are independently alkyl, alkoxy, —NO$_2$, —OH, halogen, —CN, —CF$_3$, or —OCF$_3$; and R$_8$ is H, alkyl, aryl, arylalkyl, cycloalkyl, or cycloalkylalkyl;

wherein each of the above is optionally substituted with up to 5 groups that are independently alkyl (C$_1$–C$_6$), alkoxy (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$).

In a particularly preferred embodiment, the pyrroloquinoline of the present invention is defined as:

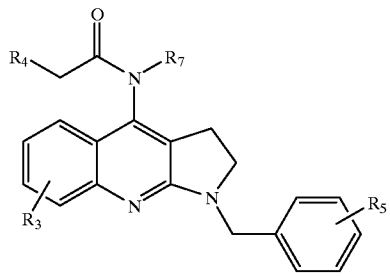

or pharmaceutically acceptable salts thereof, wherein,

R$_4$ is H, alkyl (C$_1$–C$_6$), halogen, haloalkyl, —OH, alkoxy, hydroxyalkyl, —SH, —S-alkyl, —NO$_2$, —NH$_2$, mono- or dialkylamino, aminoalkyl, mono- or dialkylamino, phenyl, or benzyl;

wherein each of the above is optionally substituted with up to 4 groups that are independently alkyl (C$_1$–C$_6$), halogen, haloalkyl, —OH, alkoxy, hydroxyalkyl, —NO$_2$, or —NR'R", wherein R' and R" are independently H or alkyl (C$_1$–C$_6$);

R$_3$ is H, alkyl (C$_1$–C$_4$), halogen, alkoxy (C$_1$–C$_4$), —CF$_3$, or —OCF$_3$;

R$_5$ is H, alkyl (C$_1$–C$_4$), halogen, alkoxy (C$_1$–C$_4$), —CF$_3$, or —OCF$_3$; and R$_7$ is H, alkyl (C$_1$–C$_6$), alkoxy, alkoxycarbonyl, preferably tertiary-butoxycarbonyl (BOC), arylalkyl, preferably benzyl, or arylalkoxycarbonyl, preferably carbobenzyloxy (Cbz), wherein each is optionally substituted with up to three groups that are independently alkyl, alkoxy, —NO$_2$, —OH, halogen, —CN, —CF$_3$, or —OCF$_3$.

More preferred embodiments of the pyrroloquinoline compounds of the present invention include (1-Benzyl-2,3-dihydro-1H-pyrrolo[2,3-b]quinolin-4-ylamino)-acetic acid ethyl ester; (1-Benzyl-2,3-dihydro-1H-pyrrolo [2,3-b] quinolin-4-yl)-(3,5-dimethoxybenzyl)-amine; N-(1-Benzyl-2,3-dihydro-1H-pyrrolo[2,3-b]quinolin-4-yl)-2-piperidin-1-yl-acetamide; N-(1-Benzyl-2,3-dihydro-1H-pyrrolo[2,3-b] quinolin-4-yl)-2-phenyl-acetamide; N-(1-Benzyl-2,3-dihydro-1H-pyrrolo[2,3-b]quinolin-4-yl)-2-fluoro-6-trifluoromethyl-benzamide; N-(1-Benzyl-2,3-dihydro-1H-pyrrolo[2,3-b]quinolin-4-yl)-4-fluoro-3-trifluoromethyl-benzamide; N-(1-Benzyl-2,3-dihydro-1H-pyrrolo[2,3-b] quinolin-4-yl)-2,3,6-trifluoro-benzamide; or pharmaceutically acceptable salts thereof.

Figure 2:
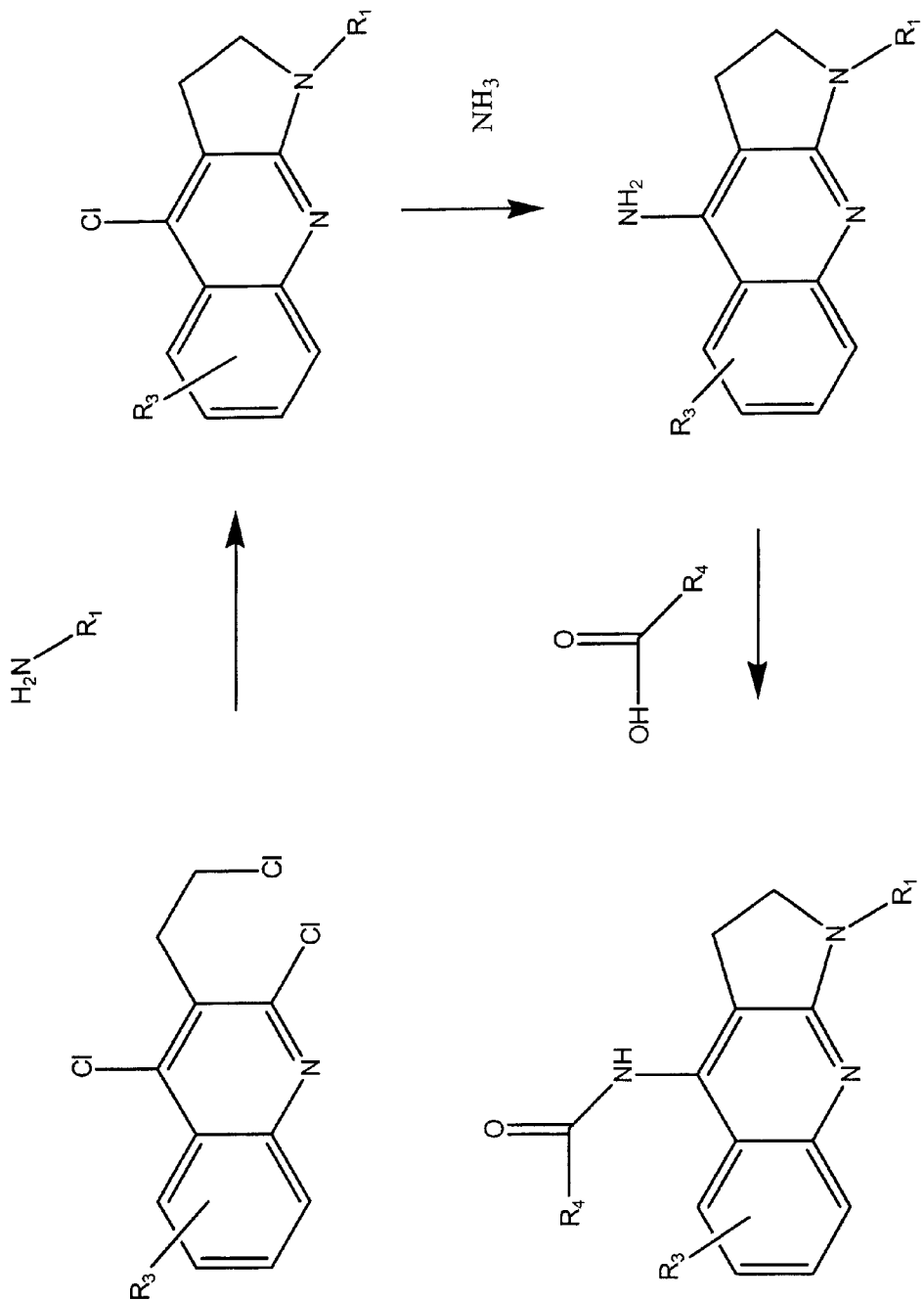
FIG. 2 illustrates one scheme for the synthesis of the pyrroloquinoline compounds of the present invention.

The pyrroloquinoline compounds of the present invention may be synthesized according to reaction scheme shown in FIG. 2. In this reaction scheme, a 2,4-dichloro-3-(β-chloroethyl) quinoline derivative, which may be prepared by treatment of the corresponding derivative of 2,3,4,5-tetrahydro-4-oxofuro[3,2-c]quinoline with phosphorus oxychloride, can be reacted with a compound containing a primary amine to form the substituted pyrrolo[2,3-b] quinoline nucleus (Tanaka et al., 1972, Chem. Pham. Bull. 20:109). Reaction with ammonia can produce substituted amino-pyrrolo[2,3-b]quinoline, which can be further reacted with carboxylate compounds to form the amide linkage indicated in FIG. 2. These reactions will occur with virtually any R$_1$-substituted primary amine and virtually any R$_4$-substituted carboxylate compound, allowing the rapid synthesis of very diverse families of pyrroloquinoline derivatives. A large number of starting materials are available from Aldrich Chemical Company and other chemical suppliers.

Figure 3:
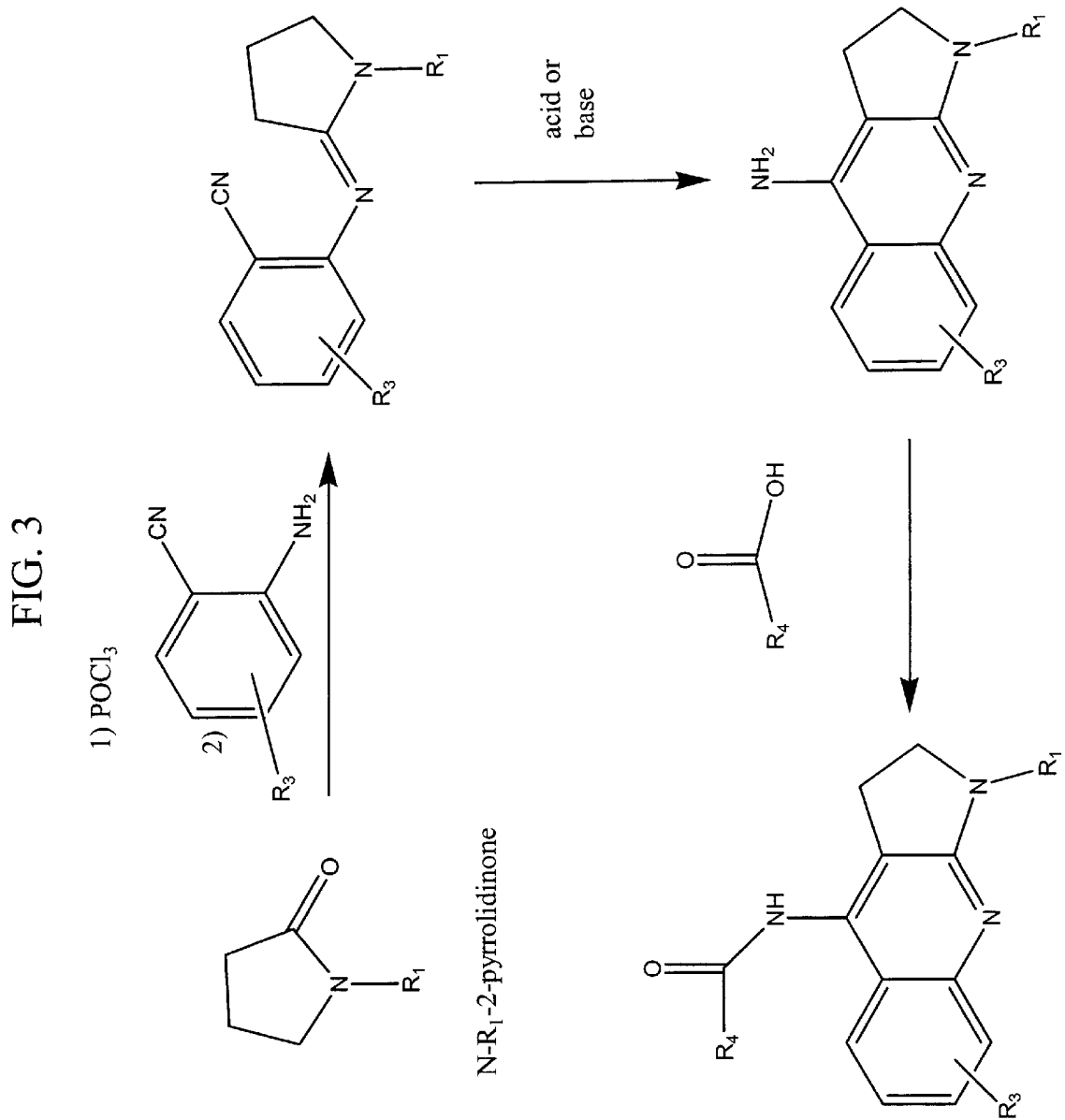
FIG. 3 illustrates another scheme for the synthesis of the pyrroloquinoline compounds of the present invention.

The pyrroloquinoline compounds of the present invention may also be synthesized according to reaction scheme shown in FIG. 3. In this reaction scheme, R$_1$-substituted pyrrolidinone can be reacted with phosphorus oxychloride, followed by reaction with R$_3$-substituted-2-cyanoaniline (European Patent Serial No. EP 430 485 to Kuroki et al.). Treatment with acid or base allows cyclization to the substituted amino pyrrolo[2,3-b]quinoline that can be further derivatized as shown in FIG. 2.

The chemical compounds of the present invention may be formulated into compositions with a biologically compatible vehicle or carrier. Such compositions may further comprise an additional transport-inhibiting compound or an additional therapeutic agent.

In one embodiment, the pharmaceutical compositions of the present invention comprise a phenoxymethyiquinoxalinone compound (I) of the formula: or a pharmaceutically acceptable salt thereof; with at least one pharmaceutically acceptable carrier or excipient, wherein

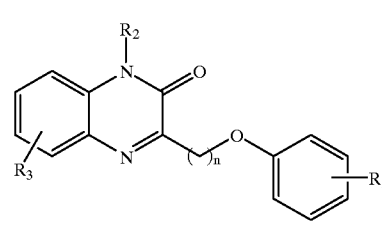

(I)

or a pharmaceutically acceptable salt thereof; with at least one pharmaceutically acceptable carrier or excipient, wherein n is an integer from 1 to 12, preferably n is 1;

R$_1$ is H, alkyl (C$_1$–C$_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$);

R$_2$ is H, alkyl (C$_1$–C$_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$);

R$_3$ is H, alkyl (C$_1$–C$_{15}$), cycloalkyl, cycloalkylalkyl, aryl, preferably phenyl, arylalkyl, preferably benzyl, heteroaryl, preferably pyridine, heteroarylalkyl, heterocycloalkyl, heterocycloalkylalkyl, halogen, haloalkyl, —OH, alkoxy, hydroxyalkyl, alkanoyl, —COOH, carboxamide, mono or dialkylaminocarboxamide, —SH, —S-alkyl, —CF$_3$, —OCF$_3$, —NO$_2$, —NH$_2$, —CO$_2$R$_8$, —OC(O)R$_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$); and R$_8$ is H, alkyl, aryl, arylalkyl, cycloalkyl, cycloalkylalkyl, heteroaryl, heteroarylalkyl, heterocycloalkyl, or heterocycloalkylalkyl;

wherein each of the above is optionally substituted with up to 5 groups that are independently alkyl (C$_1$–C$_6$), alkoxy (C$_1$–C$_6$), halogen, haloalkyl, —CF$_3$, —OCF$_3$, —OH, alkoxy, hydroxyalkyl, —CN, —CO$_2$H, —SH, —S-alkyl, —NO$_2$, or —NR'R", wherein R' and R" are independently H or alkyl (C$_1$–C$_6$).

In a more preferred embodiment, the pharmaceutical compositions of the present invention comprise a phenoxymethylquinoxalinone compounds of formula (I) wherein:

R$_1$ and R$_3$ are independently H, alkyl (C$_1$–C$_{15}$), cycloalkyl, cycloalkylalkyl, aryl, preferably phenyl, arylalkyl, preferably benzyl, halogen, haloalkyl, —OH, alkoxy, hydroxyalkyl, alkanoyl, carboxamide, mono or dialkylaminocarboxamide, —CF$_3$, —OCF$_3$, —NO$_2$, —NH$_2$, —CO$_2$R$_8$, —OC(O)R$_8$, mono- or dialkylamino, aminoalkyl, or mono- or dialkylaminoalkyl;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, or —NR'R", wherein R' and R" are independently H or alkyl (C$_1$–C$_6$);

R$_2$ is H, alkyl (C$_1$–C$_8$), cycloalkyl, cycloalkylalkyl, aryl, preferably phenyl, arylalkyl, preferably benzyl, halogen, haloalkyl, —OH, alkoxy, hydroxyalkyl, alkanoyl, carboxamide, mono or dialkylaminocarboxamide, —CO$_2$R$_8$, —OC(O)R$_8$, carbamoyl, mono or dialkylcarbamoyl, mono- or dialkylamino, aminoalkyl, or mono- or dialkylaminoalkyl;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, or —NR'R", wherein R' and R" are independently H or alkyl (C$_1$–C$_6$); and R$_8$ is H, alkyl, aryl, arylalkyl, cycloalkyl, or cycloalkylalkyl;

wherein each of the above is optionally substituted with up to 5 groups that are independently alkyl (C$_1$–C$_6$), alkoxy (C$_1$–C$_6$), halogen, —CF$_3$, —OCF$_3$, —OH, hydroxyalkyl, —CN, —CO$_2$H, or —NR'R", wherein R' and R" are independently H or alkyl (C$_1$–C$_6$).

In another more preferred embodiment, the pharmaceutical compositions of the present invention comprise a phenoxymethyiquinoxalinone compound of the formula: or a pharmaceutically acceptable salt thereof, wherein

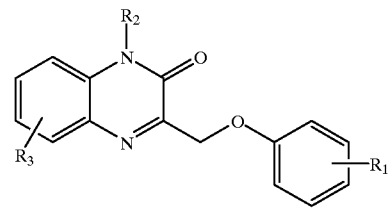

or a pharmaceutically acceptable salt thereof, wherein

R$_1$ and R$_3$ are independently H, alkyl (C$_1$–C$_{15}$), cycloalkyl, cycloalkylalkyl, aryl, preferably phenyl, arylalkyl, preferably benzyl, halogen, haloalkyl, —OH, alkoxy, hydroxyalkyl, alkanoyl, carboxamide, mono or dialkylaminocarboxamide, —CF$_3$, —OCF$_3$, —NO$_2$, —NH$_2$, —CO$_2$R$_8$, —OC(O)R$_8$, mono- or dialkylamino, aminoalkyl, or mono- or dialkylaminoalkyl;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, or —NR'R", wherein R' and R" are independently H or alkyl (C$_1$–C$_6$);

R$_2$ is H, alkyl (C$_1$–C$_8$), cycloalkyl, cycloalkylalkyl, aryl, preferably phenyl, arylalkyl, preferably benzyl, halogen, haloalkyl, —OH, alkoxy, hydroxyalkyl, alkanoyl, carboxamide, mono or dialkylaminocarboxamide, —CO$_2$R$_8$, —OC(O)R$_8$, carbamoyl, mono or dialkylcarbamoyl, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, or —NR'R", wherein R' and R" are independently H or alkyl ($C_1$–$C_6$); and $R_8$ is H, alkyl, aryl, arylalkyl, cycloalkyl, or cycloalkylalkyl;

wherein each of the above is optionally substituted with up to 5 groups that are independently alkyl ($C_1$–$C_6$), alkoxy ($C_1$–$C_6$), halogen, —$CF_3$, —$OCF_3$, —OH, hydroxyalkyl, —CN, —$CO_2$H, or —NR'R", wherein R' and R" are independently H or alkyl ($C_1$–$C_6$).

An even more preferred embodiment of the pharmaceutical compositions of the present invention comprise 1,3-Dimethyl-1H-quinoxalin-2-one; 1-Methyl-3-phenoxymethyl-1H-quinoxalin-2-one; 3-(4-Cyano-phenoxymethyl)-1-methyl-1H-quinoxalin-2-one; 3-(3-tert-Butyl-phenoxymethyl)-1-methyl-1H-quinoxalin-2-one; 3-(4-Benzoyl-phenoxymethyl)-1-methyl-1H-quinoxalin-2-one; 3-Methoxy-4-(4-methyl-3-oxo-3,4-dihydroquinoxalin-2-yl-methoxy)-benzoyl methyl ester; 2-(4-Methyl-3-oxo-3,4-dihydroquinoxalin-2-yl-methoxy)-N-phenylbenzamide; 4-(4-Methyl-3-oxo-3,4-dihydroquinoxalin-2-ylmethoxy)-benzoyl ethyl ester; 2-(4-Benzyl-3-oxo-3,4-dihydroquinoxalin-2-ylmethoxy)-N-phenylbenzamide; or pharmaceutically acceptable salts thereof; with at least one pharmaceutically acceptable carrier or excipient.

Particularly preferred embodiments of the pharmaceutical compositions of the present invention comprise 2-(4-Methyl-3-oxo-3,4-dihydroquinoxalin-2-yl-methoxy)-N-phenyl-benzamide or 2-(4-Benzyl-3-oxo-3,4-dihydroquinoxalin-2-ylmethoxy)-N-phenylbenzamide; with at least one pharmaceutically acceptable carrier or excipient.

In another embodiment, the pharmaceutical compositions of the present invention comprise a compound of the formula:

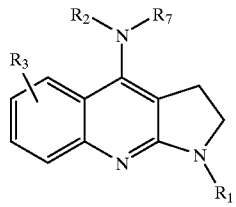

or a pharmaceutically acceptable salt thereof; with at least one pharmaceutically acceptable carrier or excipient, wherein $R_1$ is H, alkyl ($C_1$–$C_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, alkanoyl, arylalkanoyl, —COOH, carboxamide, mono or dialkylaminocarboxamide, —SH, —S-alkyl, —$CF_3$, —$OCF_3$, —$NO_2$, —$NH_2$, —$CO_2R_8$, —OC(O)$R_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, —$CO_2$H, —SH, —S-alkyl, —$NO_2$, or —NR'R", wherein R' and R" are independently H or alkyl ($C_1$–$C_6$);

$R_2$ is H, alkyl ($C_1$–$C_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, —COOH, carboxamide, mono or dialkylaminocarboxamide, —SH, —S-alkyl, —$CF_3$, —$OCF_3$, —$NO_2$, —$NH_2$, —$CO_2R_8$, —OC(O)$R_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, —$CO_2$H, —SH, —S-alkyl, —$NO_2$, or —NR'R", wherein R' and R" are independently H or alkyl ($C_1$–$C_6$); or $R_2$ is:

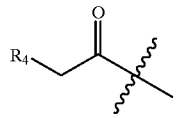

wherein $R_4$ represents H, alkyl ($C_1$–$C_6$), halogen, haloalkyl, —OH, alkoxy, hydroxyalkyl, —SH, —S-alkyl, —$NO_2$, —$NH_2$, mono- or dialkylamino, aminoalkyl, mono- or dialkylaminoalkyl, heterocycloalkyl, preferably pyrrolyl, morpholinyl, thiomorpholinyl, piperidyl, or piperazyl, heterocycloalkylalkyl, aryl, preferably phenyl, or arylalkyl, preferably benzyl, heteroaryl, or heteroarylalkyl;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, —$CO_2$H, —SH, —S-alkyl, —$NO_2$, or —NR'R", wherein R' and R" are independently H or alkyl ($C_1$–$C_6$);

$R_3$ is H, alkyl ($C_1$–$C_{15}$), cycloalkyl, cycloalkylalkyl, aryl, arylalkyl, heteroaryl, heteroarylalkyl, heterocycloalkyl, heterocycloalkylalkyl, halogen, haloalkyl, —OH, alkoxy, hydroxyalkyl, —COOH, carboxamide, mono or dialkylaminocarboxamide, —SH, —S-alkyl, —$CF_3$, —$OCF_3$, —$NO_2$, —$NH_2$, —$CO_2R_8$, —OC(O)$R_8$, carbamoyl, mono or dialkylcarbamoyl, mono- or dialkylamino, aminoalkyl, mono- or dialkylaminoalkyl, thiocarboxamide, or mono or dialkylthiocarboxamide;

wherein each of the above is optionally substituted with up to 5 groups that are independently alkyl ($C_1$–$C_6$), halogen, haloalkyl, —$CF_3$, —$OCF_3$, —OH, alkoxy, hydroxyalkyl, —CN, —$CO_2$H, —SH, —S-alkyl, —$NO_2$, or —NR'R", wherein R' and R" are independently H or alkyl ($C_1$–$C_6$);

$R_7$ is H, alkyl ($C_1$–$C_6$), alkoxy, alkoxycarbonyl, preferably tertiary-butoxycarbonyl (BOC), arylalkyl, preferably benzyl, or arylalkoxycarbonyl, preferably carbobenzyloxy (Cbz), wherein each is optionally substituted with up to three groups that are independently alkyl, alkoxy, —$NO_2$, —OH, halogen, —CN, —$CF_3$, or —$OCF_3$; and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein each of the above is optionally substituted with up to 5 groups that are independently alkyl ($C_1$–$C_6$), alkoxy ($C_1$–$C_6$), halogen, haloalkyl, —$CF_3$, —$OCF_3$, —OH, alkoxy, hydroxyalkyl, —CN, —$CO_2H$, —SH, —S-alkyl, —$NO_2$, or —NR'R", wherein R' and R" are independently H or alkyl ($C_1$–$C_6$).

In a preferred embodiment, the pharmaceutical compositions of the present invention comprise a pyrroloquinoline compound of the formula:

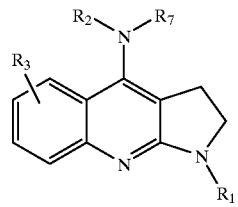

with at least one pharmaceutically acceptable carrier or excipient, wherein $R_1$ is H, alkyl ($C_1$–$C_6$), alkoxy, cycloalkyl, cycloalkylalkyl, alkanoyl, benzyl, or benzoyl;

wherein each of the above is optionally substituted with up to 5 groups that are independently alkyl ($C_1$–$C_6$), halogen, haloalkyl, —OH, alkoxy, hydroxyalkyl, —SH, —S-alkyl, —$NO_2$, or —NR'R", wherein R' and R" are independently H or alkyl ($C_1$–$C_6$);

$R_2$ is H, alkyl ($C_1$–$C_6$), cycloalkyl, cycloalkylalkyl, arylalkyl, halogen, haloalkyl, —OH, alkoxy, hydroxyalkyl, carboxamide, mono or dialkylcarboxamido, aminoalkyl, mono- or dialkylaminoalkyl, phenyl, or benzyl;

wherein each of the above is optionally substituted with up to 5 groups that are independently alkyl ($C_1$–$C_6$), halogen, haloalkyl, —OH, alkoxy, hydroxyalkyl, —SH, —S-alkyl, —$NO_2$, or —NR'R", wherein R' and R" are independently H or alkyl ($C_1$–$C_6$); or $R_2$ is:

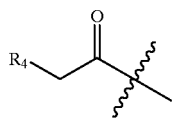

wherein $R_4$ represents H, alkyl ($C_1$–$C_6$), halogen, haloalkyl, —OH, alkoxy, hydroxyalkyl, —SH, —S-alkyl, —$NO_2$, —$NH_2$, mono- or dialkylamino, aminoalkyl, mono- or dialkylaminoalkyl, pyrrolyl, piperidyl, piperazyl, phenyl, or benzyl;

wherein each of the above is optionally substituted with up to 5 groups that are independently alkyl ($C_1$–$C_6$), halogen, haloalkyl, —OH, alkoxy, hydroxyalkyl, —SH, —S-alkyl, —$NO_2$, or —NR'R", wherein R' and R" are independently H or alkyl ($C_1$–$C_6$);

$R_3$ is H, alkyl ($C_1$–$C_{15}$), cycloalkyl, cycloalkylalkyl, halogen, haloalkyl, —OH, alkoxy, hydroxyalkyl, carboxamide, mono or dialkylcarboxamide, —$CO_2R_8$, —$CF_3$, —$OCF_3$, —$NO_2$, —$NH_2$, aminoalkyl, mono- or dialkylaminoalkyl, phenyl, or benzyl;

wherein each of the above is optionally substituted with up to 5 groups that are independently alkyl ($C_1$–$C_6$), halogen, haloalkyl, —OH, alkoxy, hydroxyalkyl, —SH, —S-alkyl, —$NO_2$, or —NR'R", wherein R' and R" are H or alkyl ($C_1$–$C_6$);

$R_7$ is H, alkyl ($C_1$–$C_6$), alkoxy, alkoxycarbonyl, preferably tertiary-butoxycarbonyl (BOC), arylalkyl, preferably benzyl, or arylalkoxycarbonyl, preferably carbobenzyloxy (Cbz), wherein each is optionally substituted with up to three groups that are independently alkyl, alkoxy, —$NO_2$, —OH, halogen, —CN, —$CF_3$, or —$OCF_3$; and $R_8$ is H, alkyl, aryl, arylalkyl, cycloalkyl, or cycloalkylalkyl;

wherein each of the above is optionally substituted with up to 5 groups that are independently alkyl ($C_1$–$C_6$), alkoxy ($C_1$–$C_6$), halogen, haloalkyl, —$CF_3$, —$OCF_3$, —OH, alkoxy, hydroxyalkyl, —CN, —$CO_2H$, —SH, —S-alkyl, —$NO_2$, or —NR'R", wherein R' and R" are independently H or alkyl ($C_1$–$C_6$).

In a particularly preferred embodiment, the pharmaceutical compositions of the present invention comprise a pyrroloquinoline compound of the formula:

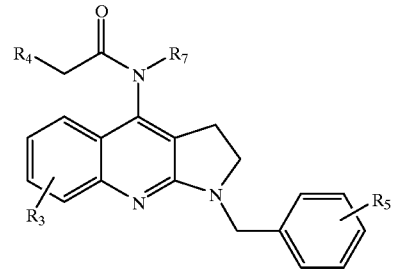

or a pharmaceutically acceptable salt thereof; with at least one pharmaceutically acceptable carrier or excipient wherein $R_4$ represents H, alkyl ($C_1$–$C_6$), halogen, haloalkyl, —OH, alkoxy, hydroxyalkyl, —SH, —S-alkyl, —$NO_2$, —$NH_2$, mono- or dialkylamino, aminoalkyl, mono- or dialkylamino, pyrrolyl, piperidyl, piperazyl, phenyl, or benzyl;

wherein each of the above is optionally substituted with up to 5 groups that are independently alkyl ($C_1$–$C_6$), halogen, haloalkyl, —OH, alkoxy, hydroxyalkyl, —SH, —S-alkyl, —$NO_2$, or —NR'R", wherein R' and R" are independently H or alkyl ($C_1$–$C_6$);

$R_3$ is H, alkyl ($C_1$–$C_4$), halogen, alkoxy ($C_1$–$C_4$), —$CF_3$, or —$OCF_3$;

$R_5$ is H, alkyl ($C_1$–$C_4$), halogen, alkoxy ($C_1$–$C_4$), —$CF_3$, or —$OCF_3$; and $R_7$ is H, alkyl ($C_1$–$C_6$), alkoxy, alkoxycarbonyl, preferably tertiary-butoxycarbonyl (BOC), arylalkyl, preferably benzyl, or arylalkoxycarbonyl, preferably carbobenzyloxy (Cbz), wherein each is optionally substituted with up to three groups that are independently alkyl, alkoxy, —$NO_2$, —OH, halogen, —CN, —$CF_3$, or —$OCF_3$.

More preferred embodiments of these pharmaceutical compositions comprise (1-Benzyl-2,3-dihydro-1H-pyrrolo [2,3-b]quinolin-4-ylamino)-acetic acid ethyl ester; (1-Benzyl-2,3-dihydro-1H-pyrrolo [2,3-b]quinolin-4-yl)-(3,5-dimethoxy-benzyl)-amine; N-(1-Benzyl-2,3-dihydro-1H-pyrrolo[2,3-b]quinolin-4-yl)-2-piperidin-1-yl-acetamide; N-(1-Benzyl-2,3-dihydro-1H-pyrrolo[2,3-b]quinolin-4-yl)-2-phenyl-acetamide; N-(1-Benzyl-2,3-dihydro-1H-pyrrolo [2,3-b]quinolin-4-yl)-2-fluoro-6-trifluoromethyl-benzamide; N-(1-Benzyl-2,3-dihydro-1H-pyrrolo [2,3-b] quinolin-4-yl)-4-fluoro-3-trifluoromethyl-benzamide; N-(1-

Benzyl-2,3-dihydro-1H-pyrrolo[2,3-b]quinolin-4-yl)-2,3,6-trifluoro-benzamide; or pharmaceutically acceptable salts thereof; with at least one pharmaceutically acceptable carrier or excipient.

Pharmaceutically acceptable salts of the chemical compounds of the present invention, which also have chemosensitizing activity (e.g., the hydrochloride or sodium salts), may be prepared following procedures that are familiar to those skilled in the art.

The chemosensitizing pharmaceutical compositions of the present invention comprise one or more of the chemical compounds of the present invention, as active ingredients, in combination with a pharmaceutically acceptable carrier, medium, or auxiliary agent.

The pharmaceutical compositions of the present invention may be prepared in various forms for administration, including tablets, caplets, pills or dragees, or can be filled in suitable containers, such as capsules, or, in the case of suspensions, filled into bottles. As used herein "pharmaceutically acceptable carrier medium" includes any and all solvents, diluents, or other liquid vehicle; dispersion or suspension aids; surface active agents; preservatives; solid binders; lubricants and the like, as suited to the particular dosage form desired. Various vehicles and carriers used in formulating pharmaceutical compositions and known techniques for the preparation thereof are disclosed in *Remington's Pharmaceutical Sciences* (A. Osol et al. eds., 15th ed. 1975). Except insofar as any conventional carrier medium is incompatible with the chemical compounds of the present invention, such as by producing any undesirable biological effect or otherwise interacting in a deleterious manner with any other component of the pharmaceutical composition, the use of the carrier medium is contemplated to be within the scope of this invention.

In the pharmaceutical compositions of the present invention, the active agent may be present in an amount of at least 1% and not more than 95% by weight, based on the total weight of the composition, including carrier medium or auxiliary agents. Preferably, the proportion of active agent varies between 1% to 70% by weight of the composition. Pharmaceutical organic or inorganic solid or liquid carrier media suitable for enteral or parenteral administration can be used to make up the composition. Gelatin, lactose, starch, magnesium, stearate, talc, vegetable and animal fats and oils, gum polyalkylene glycol, or other known excipients or diluents for medicaments may all be suitable as carrier media.

The pharmaceutical compositions of the present invention may be administered using any amount and any route of administration effective for increasing the therapeutic efficacy of drugs. Thus the expression "therapeutically effective amount," as used herein, refers to a sufficient amount of the chemosensitizing agent to provide the desired effect against target cells. The exact amount required will vary from subject to subject, depending on the species, age, and general condition of the subject; the particular chemosensitizing agent; its mode of administration; and the like.

The pharmaceutical compounds of the present invention are preferably formulated in dosage unit form for ease of administration and uniformity of dosage. "Dosage unit form," as used herein, refers to a physically discrete unit of therapeutic agent appropriate for the animal to be treated. Each dosage should contain the quantity of active material calculated to produce the desired therapeutic effect either as such, or in association with the selected pharmaceutical carrier medium. Typically, the pharmaceutical composition will be administered in dosage units containing from about 0.1 mg to about 10,000 mg of the agent, with a range of about 1 mg to about 1000 mg being preferred.

The pharmaceutical compositions of the present invention may be administered orally or paternally, such as by intramuscular injection, intraperitoneal injection, or intravenous infusion. The pharmaceutical compositions may be administered orally or parenterally at dosage levels of about 0.1 to about 1000 mg/kg, and preferably from about 1 to about 100 mg/kg, of animal body weight per day, one or more times a day, to obtain the desired therapeutic effect.

Although the pharmaceutical compositions of the present invention can be administered to any subject that can benefit from the therapeutic effects of the compositions, the compositions are intended particularly for the treatment of diseases in humans.

The pharmaceutical compositions of the present invention will typically be administered from 1 to 4 times a day, so as to deliver the daily dosage as described herein. Alternatively, dosages within these ranges can be administered by constant infusion over an extended period of time, usually 1 to 96 hours, until the desired therapeutic benefits have been obtained. However, the exact regimen for administration of the chemical compounds and pharmaceutical compositions described herein will necessarily be dependent on the needs of the animal being treated, the type of treatments being administered, and the judgment of the attending physician.

The pharmaceutical compositions of the present invention can be used in various protocols for treating animals. In one embodiment of the methods of the present invention, drug transport from target cells or tissues in an animal undergoing chemotherapy is inhibited by administering to the animal a pharmaceutical composition of the present invention in an amount effective to inhibit drug transport from the target cells or tissues of the animal. In another embodiment of the methods of the present invention, drug resistance in an animal undergoing chemotherapy is prevented by administering to the animal a pharmaceutical composition of the present invention in an amount effective to attenuate drug resistance.

Additionally, a chemical compound of the present invention may be administered in combination with an anticancer compound that is effective in sensitizing drug resistant tumor cells, the amount of the combination being effective to enhance the therapeutic efficacy of the anticancer compound. Anticancer compounds that may be suitable include, for example, dihydropyridines, thioxanthenes, phenothiazines, cyclosporins, acridonecarboxamides, verapamil, cyclosporin A, PSC 833, tamoxifen, quinidine, quinine, bepridil, ketoconazole, megestrol acetate, and estramustine. Other anticancer compounds that are found to inhibit drug efflux, including newly discovered anticancer compounds, are within the scope of the combinations of the present invention.

In view of the beneficial effect of reversing MDR, as produced by the chemical compounds of the present invention, it is anticipated that these compounds will be useful not only for therapeutic treatment following the onset of MDR, but also for the prevention of MDR in animals about to undergo chemotherapy for the first time. The dosages described herein will be essentially the same whether the pharmaceutical compositions of the present invention are being administered for the treatment or prevention of MDR.

The chemical compounds and pharmaceutical compositions of the present invention may also be useful for enhancing the therapeutic efficacy of other drugs. In view of the roles of transport proteins in impairing drug delivery to several sites within the body, these compounds and compositions will have utility in increasing drug delivery to the central nervous system, the eye, the testes, the liver, the adrenal gland, the pancreas and leukocytes. Additionally, inhibition of transport proteins in the intestine by compounds and compositions of the present invention will have utility in enhancing the bioavailability of orally delivered therapeutic agents. Furthermore, the compounds and compositions of this invention may be used to enhance the therapeutic efficacy of anti-infection drugs toward organisms that are resistant to these drugs. In each of these cases, at least one chemical compound or pharmaceutical composition of the present invention in combination with at least one therapeutic drug would be administered to an animal in an amount effective to enhance the therapeutic efficacy of the therapeutic drug.

In one embodiment of the methods of the present invention, the therapeutic efficacy of an antiproliferative drug in target cells or tissues of an animal is enhanced by administering to the animal a pharmaceutical composition of the present invention in an amount effective to enhance delivery of the antiproliferative drug to the target cells or tissues of the animal.

In another embodiment of the methods of the present invention, the therapeutic efficacy of an anti-infective agent in an animal is enhanced by administering to the animal a pharmaceutical composition of the present invention in an amount effective to inhibit drug transport from an infectious agent in the animal.

In still another embodiment of the methods of the present invention, the delivery of a therapeutic agent to target cells or tissues of an animal is enhanced by administering to the animal a pharmaceutical composition of the present invention in an amount effective to enhance delivery of the therapeutic agent to the target cells or tissues of the animal. In more preferred embodiments of these methods, the delivery of a therapeutic agent to the brain, testes, eye, or leukocytes is enhanced.

In yet another embodiment of the methods of the present invention, the absorption of an orally-delivered therapeutic agent in an animal is enhanced by administering to the animal a pharmaceutical composition of the present invention in an amount effective to enhance drug transport across the gastrointestinal tract.

The Examples, which follow, are illustrative of specific embodiments of the invention, and various uses thereof. They are set forth for explanatory purposes only, and are not to be taken as limiting the invention.

EXAMPLE 1

Synthesis of Phenoxymethylquinoxalinone Compounds

The reagents and solvents that were used to synthesize the phenoxymethylquinoxalinone compounds of the present invention were obtained from Aldrich, Acros, Fisher, or VWR. Reaction progress was monitored by analytical thin-layer chromatography (TLC). Silica gel used in flash chromatography was 60–200 mesh. Infrared Spectra were measured with an Avatar 360 ESP spectrometer and are expressed in reciprocal centimeters. $^1$H NMR and $^{13}$C NMR spectra were obtained on a Bruker 200 MHz spectrometer. Chemical shifts are reported in ppm downfield from Me$_4$Si. J values are given in Hz.

A particularly preferred embodiment of the phenoxymethylquinoxalinone compounds of the present invention, 2-(4-Methyl-3-oxo-3,4-dihydroquinoxalin-2-yl-methoxy)-N-phenylbenzamide, was synthesized as follows. The compound 1,3-Dimethyl-1H-quinoxalin-2-one (Compound A) was prepared by dissolving N-methyl-1,2-phenylenediamine (6.68 g, 54.7 mmol) and pyruvic acid (3.8 mL, 54.7 mmol) in ethanol (230 mL) and warming the mixture to 50° C. The color changed dramatically from a dark, cloudy brown to clear orange. Ethanol was evaporated and the crude product was filtered through a silica bed with CH$_2$Cl$_2$/EtOAc (1:1) to give 7.36 g of product as a yellow solid (mp. 75–77° C., 42.3 mmol, 77.2%). FT-IR (KBr): 3075–2975 cm (aromatic CR), 2950–2850 (aliphatic CR), 1650 (C=O), 1600 (C=N). $^1$H-NMR (CDCl$_3$): δ 7.80 (d, 1H, J=7.9 Hz), 7.52 (t, 1H, J=7.8 Hz), 7.33 (m, 2H), 3.70 (s, 3H), 2.59 (s, 3H).

The compound 3-Bromomethyl-1H-1-methyl-quinoxalin-2-one (Compound B) was prepared by dissolving Compound A (133 mg, 0.763 mmol) in CCl$_4$ (10 mL), adding N-bromosuccinimide (144 mg, 0.809 mmol) and benzoyl peroxide (0.4 mg, 0.002 mmol), and heating the mixture to reflux. After 10.5 hours, thin-layer chromatography (TLC; silica, 40% EtOAc/Hex) showed the reaction to be complete. The reaction was cooled to room temperature and filtered through a plug of silica with 40% EtOAc/Hex. Purification of the crude product by radial chromatography (silica, 40% EtOAc/Hex) gave 71 mg of pure product (mp. 180–182° C. [dec.], 0.28 mmol, 49%). FT-IR (KBr): 3100–3025 cm$^{-1}$ (aromatic CH), 2975–2875 (aliphatic CH), 1740 (C=O), 1650 (C=N). $^1$H-NMR (CDCl$_3$): δ 7.87 (d, 1H, J=8.0 Hz), 7.61 (t, 1H, J=7.3 Hz), 7.41–7.33 (m, 2H), 4.66 (s, 2H), 3.74 (s, 3H). $^{13}$C-NMR (CDCl$_3$): δ 155.2, 153.9, 134.0, 132.7, 131.4, 130.7, 124.2, 114.0, 29.5.

The 3-(phenoxymethyl)-1H-1-methyl-quinoxalin-2-one compounds were prepared by dissolving Compound B (100 mg, 0.395 mmol) and a specific phenol (0.395 mmol) in CHCl$_3$ (10 mL). A solution of NaOH (23.7 mg, 0.593 mmol) and benzyltriethylammonium chloride (9 mg, 0.040 mmol) in H$_2$O (10 mL) was added and the mixture stirred rapidly while heating to 50° C. The progress of the reaction was monitored by TLC (silica, 40% EtOAc/Hex). The mixture was then cooled to room temperature, the aqueous layer was extracted with fresh CHCl$_3$ (2×10 mL), the combined chloroform extracts were washed with brine (10 mL), and the product was dried over Na$_2$SO$_4$. Evaporation of the solvent, followed by filtration through a plug of silica with 40% EtOAc/Hex yielded a crude product. Purification by radial chromatography (silica, 40% EtOAc/Hex) yielded pure product.

A resulting pure product, 2-(4-Methyl-3-oxo-3,4-dihydroquinoxalin-2-yl-methoxy)-N-phenylbenzamide, was a yellow solid (mp. 148° C. [dec.], 43%). FT-IR (KBr): 3315 cm$^{-1}$ (amide NH), 3040 (aromatic CH), 2916 (aliphatic CH), 1656 (amide C=O), 1643 (C=O), 1598 (C=N). $^1$H-NMR (CDCl$_3$): δ 8.31 (dd, 1H, J=1.8, 7.8 Hz), 7.80–7.05 (m, 13H), 5.59 (s, 2H), 3.76 (s, 3H).

EXAMPLE 2

Reversal of P-gp-Mediated or MRP-Mediated MDR by Phenoxymethylquinoxalinones

The ability of the phenoxymethylquinoxalinone compounds of the present invention to reverse P-gp-mediated or MRP-mediated MDR was analyzed using MCF-7 human breast carcinoma cells; NCI/ADR cells, an MDR cell line that over-expresses P-gp (Fairchild et al., 1987, *Cancer Res.* 47:5141–48), but not MRP; and MCF-7/VP cells, a cell line that expresses MRP (Schneider et al., 1994, *Cancer Res.* 54:152–58), but not P-gp.

Reversal of P-gp-mediated MDR was examined by first plating NCI/ADR cells into 96-well tissue culture plates at approximately 15% confluency and incubating the cells for 24 hours to allow for attachment. The cells were then exposed to varying concentrations of phenoxymethylquinoxalinone compounds in the absence or presence of 50 nM vinblastine for 48 hours as described previously (Smith et al., 1994, *Oncology Res.* 6:211–18; Smith et al., 1995, *Mol. Pharmacol.* 47:241–47). Cell survival was assayed using the sulforhodamine B binding assay (Skehan et al., 1990, *J. Natl. Cancer Inst.* 82:1107–12). The percentage of cells that died following treatment was calculated as a percent decrease in sulforhodamine B binding as compared with control cultures. Control cultures were exposed to equivalent amounts of ethanol (as the solvent control), which did not modulate the growth or drug-sensitivity of these cells at the doses used. Inhibition of P-gp was manifested as the ability of the compound to enhance the cytotoxicity of vinblastine toward NCI/ADR cells. To assess the toxicity of the compounds toward drug-sensitive cells, the effects of the compounds on the growth of drug-sensitive MCF-7 cells were determined using the same methods.

Reversal of MRP-mediated MDR was examined by plating MCF-7/VP cells as described above and exposing the cells to varying concentrations of phenoxymethylquinoxalinone compounds in the absence or presence of 1 nM vincristine for 48 hours. Cell survival was assayed as described above. The percentage of cells that died following treatment was calculated as described above. Inhibition of MRP was manifested as the ability of the compound to enhance the cytotoxicity of vincristine toward MCF-7/VP cells.

The results obtained for twenty-two phenoxymethylquinoxalinone compounds are shown in Table I. Tested phenoxymethylquinoxalinone compounds were found to have an intrinsic cytotoxicity towards MCF-7 cells. Cytotoxicity is expressed as the concentration of phenoxymethylquinoxalinone compound required to kill 50% of the cells. In several cases, the maximum solubility of the compound was less than the $IC_{50}$. While toxicity toward cultured cancer cells is a typical and desired property for drugs having utility in the treatment of cancer, it is desirable that chemosensitizing compounds have low intrinsic toxicity. The phenoxymethylquinoxalinone compounds that were examined were found to have low cytotoxicity, with $IC_{50}$ values of >20 $\mu$M, and in some cases near 100 $\mu$M (Table I).

The P-gp antagonism score was calculated by dividing the percent survival of NCI/ADR cells treated with the compound alone by the percent survival of NCI/ADR cells treated with the compound in the presence of 50 nM vinblastine. Chemosensitization is indicated by a score of more than 1.0. Several of the phenoxymethylquinoxalinone compounds that were tested demonstrated this property (Table I).

The MRP antagonism score was calculated by dividing the percent survival of MCF-7/VP cells treated with the compound alone by the percent survival of MCF-7/VP cells treated with the compound in the presence of 1 nM vincristine. Chemosensitization is indicated by a score greater than 1.0. None of the phenoxymethylquinoxalinone compounds that were tested demonstrated this property (Table I). Thus, a number of the phenoxymethylquinoxalinone compounds that were tested were found to be effective inhibitors of P-gp, but not MRP.

Figure 4A:
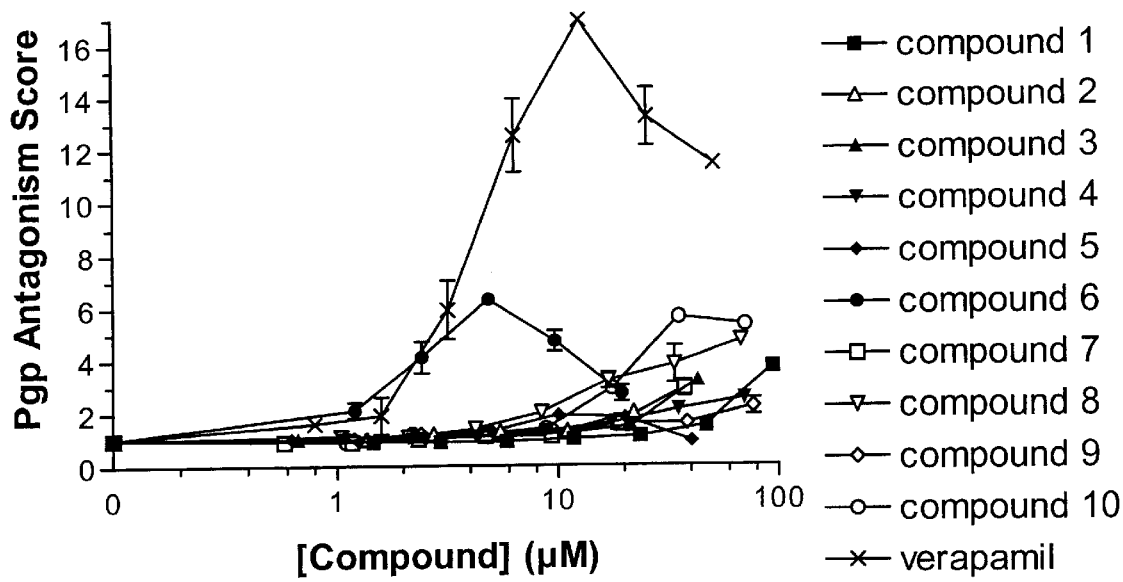
FIGS. 4A–4B illustrate the antagonism of P-gp by verapamil and phenoxymethylquinoxalinone compounds.
Figure 4B:
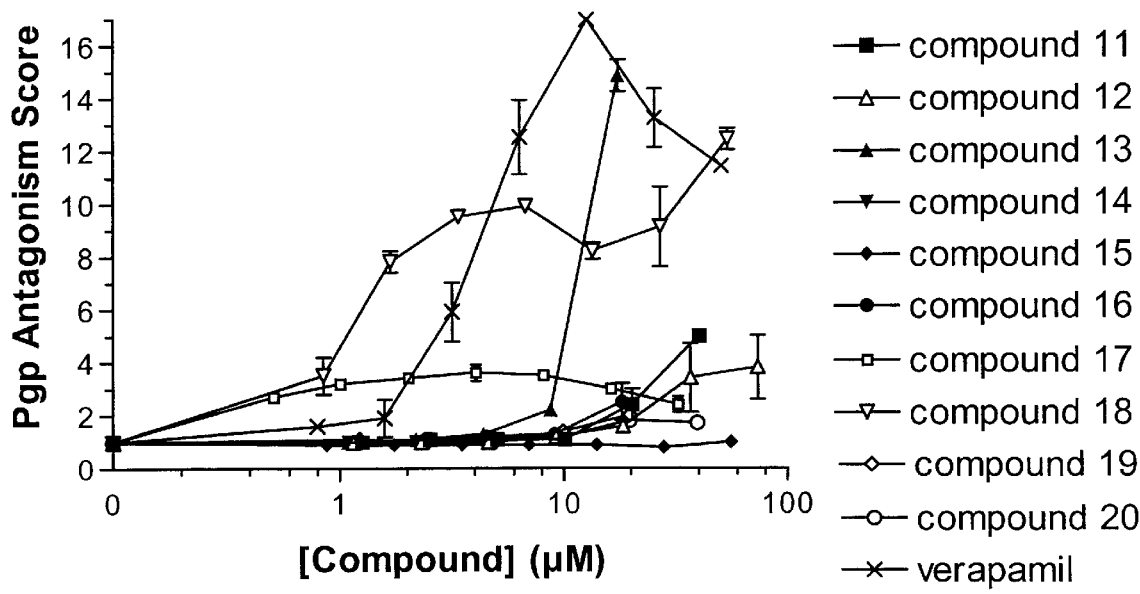
Figure 5A:
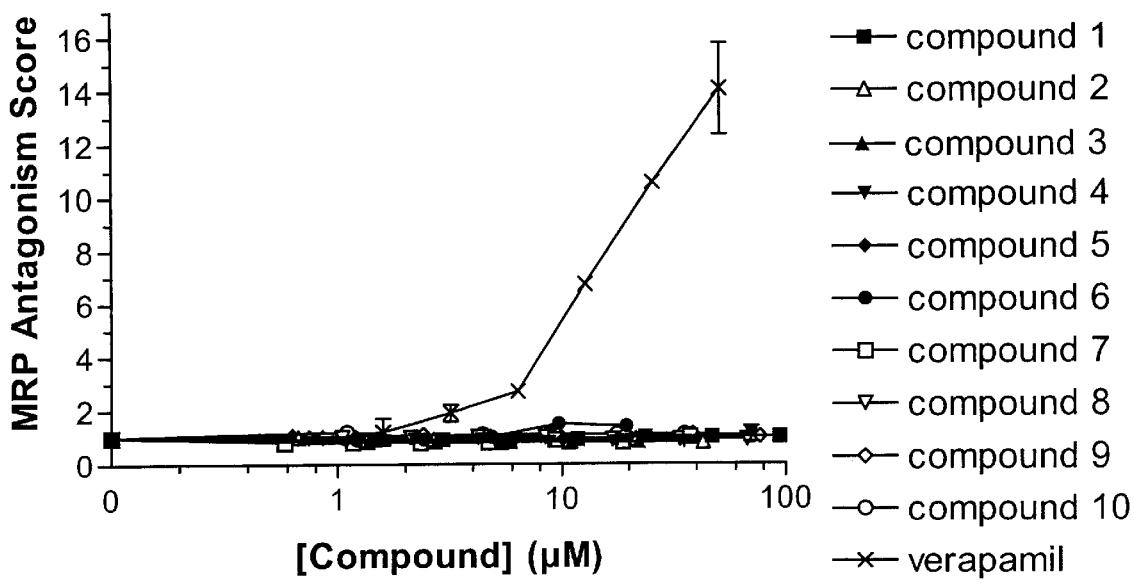
FIGS. 5A–5B illustrate the lack of antagonism of MRP1 by phenoxymethylquinoxalinone compounds.
Figure 5B:
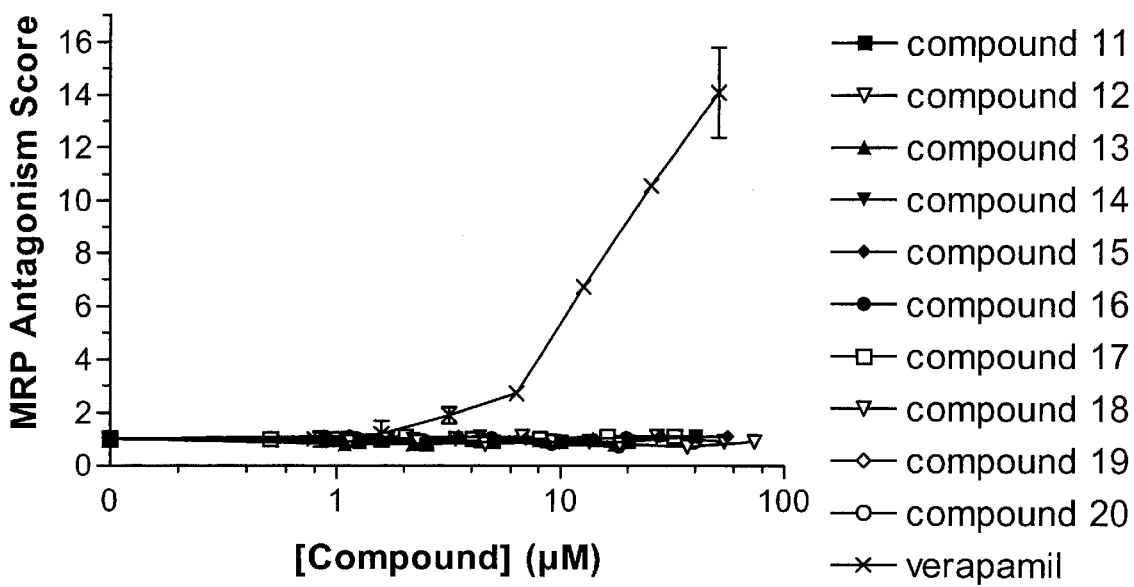

Similar experiments were conducted using verapamil or one of the particularly preferred phenoxymethylquinoxalinone compounds. FIGS. 4A–4B illustrate the antagonism of P-gp by verapamil and phenoxymethylquinoxalinone compounds and FIGS. 5A–5B illustrate the lack of antagonism of MRP1 by phenoxymethylquinoxalinone compounds.

EXAMPLE 3

Synthesis of Pyrroloquinoline Compounds

The reagents and solvents that were used to synthesize the pyrroloquinoline compounds of the present invention were obtained from Aldrich, Acros, Fisher, or VWR. Reaction progress was monitored by analytical thin-layer chromatography (TLC). Silica gel used in flash chromatography was 60–200 mesh. Infrared Spectra were measured with a Avatar 360 ESP spectrometer and are expressed in reciprocal centimeters. $^1$H NMR and $^{13}$C NMR spectra were obtained on a Bruker 200-MHz spectrometer. The chemical shifts were reported in ppm downfield from $Me_4Si$. J values are given in Hz.

Figure 6:
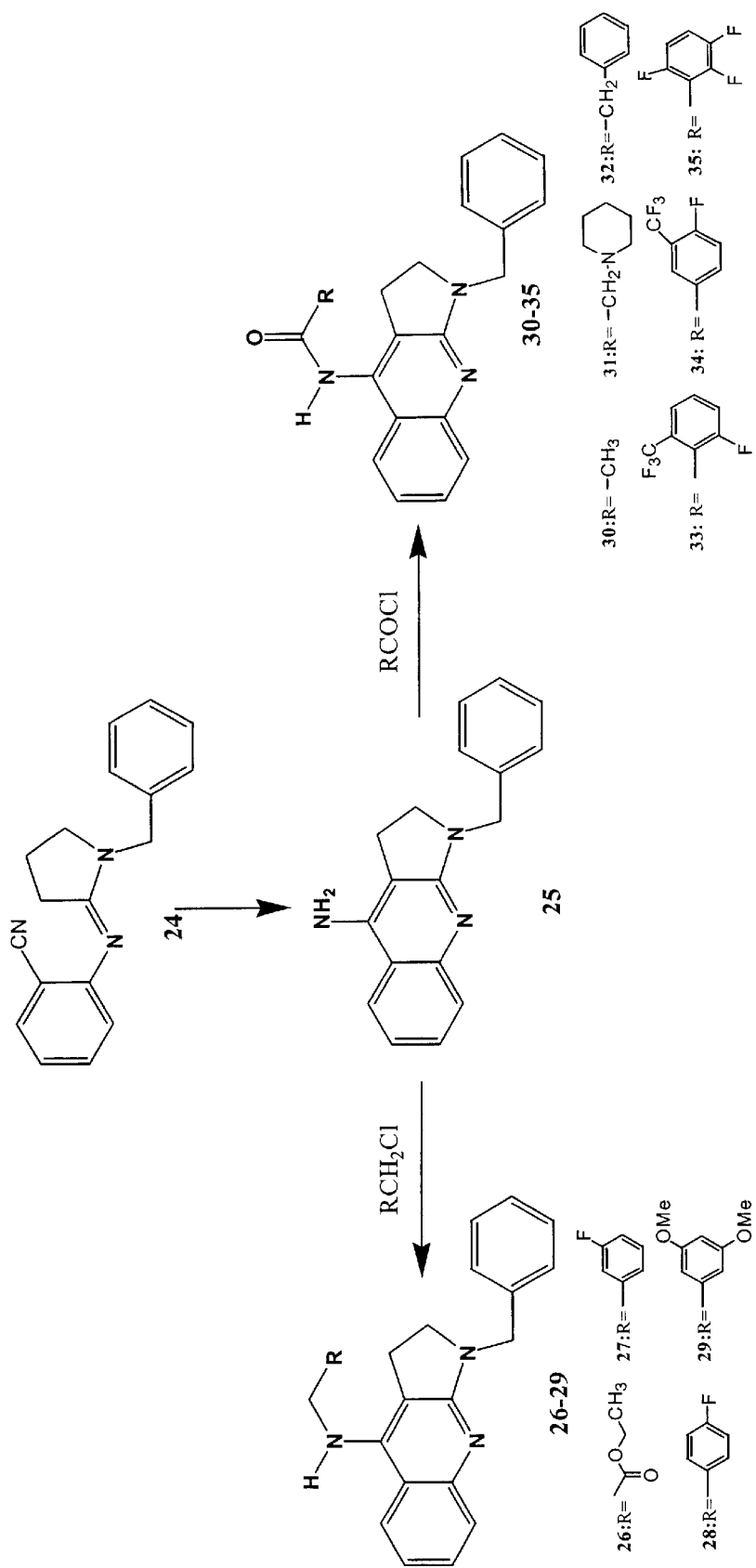
FIG. 6 illustrates another scheme for the synthesis of the pyrroloquinoline compounds of the present invention.

Pyrroloquinoline compounds were synthesized as follows. The compound 1-benzyl-2,3-dihydro-1H-pyrrolo[2,3-b]quinolin-4-ylamine was prepared from the cyclization of an amidine derivative, 2-(1-benzyl-pyrrolidin-2-ylideneamino)benzonitrile, which was synthesized by condensing an anthranilonitrile and 1-benzyl-2-pyrrolidinone. This compound was then reacted with potassium tert-butoxide or sodium hydride and the corresponding alkyl chloride or acyl chloride (FIG. 6).

The compound 2-(1-Benzyl-pyrrolidin-2-ylideneamino) benzonitrile (Compound 24) was synthesized by mixing chloroform (25 mL), tetrahydrofuran (25 mL), 1-benzyl-2-pyrrolidinone (5.16 g, 29.4 mmol), phosphorus oxychloride (5.2 mL) and tin(IV) chloride (1.0 mL), stirring at room temperature for 1.5 hours, and adding anthranilonitrile (3.3 g, 27.9 mmol) in portions. The mixture was then stirred at 50° C. for 5 hours under heating and ice-water (15 mL) and 10% aqueous sodium hydroxide solution was added to make weak alkaline. The organic solvent was removed under reduced pressure and the mixture was extracted with chloroform. The extract was dried over anhydrous sodium sulfate and condensed under vacuum. The crude product was purified by flash chromatography (chloroform-methanol, 100:1) to yield 7.0 g (91%) Compound 24 as slightly yellow needles; mp 59–61° C.; IR (KBr): 2217, 1628, 1439, 1279 cm$^{-1}$; $^1$H NMR (DMSO-d$_6$): $\delta$ 7.06–7.69 (m, 9H), 4.83 (s, 2H), 3.46 (t, 2H), 2.60 (t, 2H), 2.10 (m, 2H); $^{13}$C NMR (CDCl$_3$): $\delta$ 162.8, 156.3, 137.6, 133.7, 132.9, 128.7, 128.3, 127.4, 122.8, 121.7, 118.8, 105.9, 48.3, 47.3, 27.7, 19.6. Anal. Calcd. for $C_{18}H_{17}N_3$(275.35): C, 78.52; H, 6.22; N, 15.26. Found: C, 78.37; H, 6.20; N, 15.17.

The compound 1-Benzyl-2,3-dihydro-1H-pyrrolo[2,3-b] quinolin-4-ylamine (Compound 25) was synthesized by first cooling a solution of Compound 24 (37.6 g, 0.14 mol) and tetrahydrofuran (350 mL) to −35° C. under argon atmosphere and adding a solution of hexane (110 mL) and lithium diisopropylamine-tetrahydrofuran complex (0.35 mol) dropwise. The temperature of the mixture was then gradually raised to −10° C. and ice-water (30 mL) was added dropwise. Organic solvent was evaporated under reduced pressure and the mixture was extracted with chloroform. The combined organic extracts were dried with anhydrous sodium sulfate and condensed under vacuum. The residue was treated with ethanol (15 mL) and crystals precipitated. The precipitate was filtered, washed with cold ethanol and dried under vacuum to yield 14.6 g (39%) of Compound 25 as needles; mp 174–176° C.; IR (KBr): 3411, 3116, 1654, 1502, 1350, 756 cm$^{-1}$; $^1$H NMR (DMSO-d$_6$): δ 7.01–7.93 (m, 9H), 6.05 (s, 2H), 4.60 (s, 2H), 3.37 (t, 2H), 2.87 (t, 2H); $^{13}$C NMR (CDCl$_3$): δ 162.7, 149.3, 144.8, 138.8, 128.7, 128.2, 128.1, 127.2, 126.2, 121.8, 119.9, 117.6, 100.7, 48.4, 23.3. Anal. Calcd. for C$_{18}$H$_{17}$N$_3$(275.35): C, 78.52; H, 6.22; N, 15.26. Found: C, 78.07; H, 6.07; N, 15.08.

The compounds (1-Benzyl-2,3-dihydro-1H-pyrrolo[2,3-b]quinolin-4-ylamino)-acetic acid ethyl ester (Compound 26), (1-Benzyl-2,3-dihydro-1H-pyrrolo[2,3-b]quinolin-4-yl)-(3-fluoro-benzyl)-amine (Compound 27), (1-Benzyl-2,3-dihydro-1H-pyrrolo[2,3-b]quinolin-4-yl)-(4-fluoro-benzyl)-amine (Compound 28), and (1-Benzyl-2,3-dihydro-1H-pyrrolo[2,3-b]quinolin-4-yl)-(3,5-dimethoxy-benzyl)-amine (Compound 29) were synthesized by first adding potassium tert-butoxide to a solution of Compound 25 (1 mmol) in tetrahydrofuran (15 mL) at 0° C. under nitrogen atmosphere and stirring at room temperature for 1.5 hours. The reaction mixture was then added dropwise to a solution of a corresponding alkyl chloride (1 mmol) in tetrahydrofuran (10 mL) via syringe at −5° C., warmed to room temperature, and stirred for 1.5 to 3 hours. The resulting reaction mixture was poured into water (50 mL) and the solid precipitated. The precipitate was filtered, dried under vacuum, and the crude product purified by flash silica gel chromatography (chloroform-methanol) to yield Compounds 26–29 (see Table II).

Data for Compound 26 were as follows: yield 61%; mp 132–134° C.; IR (KBr): 3410, 1745, 1620, 1502, 1215 cm$^{-1}$; $^1$H NMR (CDCl$_3$): δ 7.16–7.72 (m, 9H), 4.77 (s, 2H), 4.25 (q, 2H), 3.51 (t, 2H), 3.49 (s, 2H), 3.11 (t, 2H), 1.34 (t, 3H); $^{13}$C NMR (CDCl$_3$): δ 171.1, 157.4, 139.6, 137.1, 135.5, 132.1, 128.8, 128.5, 128.3, 127.3, 126.5, 124.5, 121.7, 120.5, 61.9, 48.7, 48.0, 26.1, 24.9, 14.6. Anal. Calcd. for C$_{22}$H$_{23}$N$_3$O$_2$ (361.18): C, 73.11; H, 6.41; N, 11.63. Found: C, 73.04; H, 6.08; N, 11.90.

Date for Compound 27 were as follows: yield 65%; mp 170–171° C.; IR (KBr): 3400, 3063, 1622, 1504, 1217 cm$^{-1}$; $^1$H NMR (CDCl$_3$): δ 7.00–8.15 (m, 13H), 4.73 (s, 2H), 4.19 (s, 2H), 3.21 (t, 2H), 2.45 (t, 2H); $^{13}$C NMR (CDCl$_3$): δ 164.7, 162.5, 159.8, 149.8, 148.6, 137.8, 136.4, 133.5, 133.4, 130.4, 130.2, 128.6, 128.4, 128.2, 127.2, 126.6, 123.6, 121.7, 119.1, 115.4, 115.0, 54.5, 48.8, 47.8, 25.4. Anal. Calcd. for C$_{25}$H$_{22}$FN$_3$ (383.46): C, 78.30; H, 5.78; N, 10.96. Found: C, 78.23; H, 5.32; N, 11.21.

Data for Compound 28 were as follows: yield 80%; mp 167–169° C.; IR (KBr): 3405, 1620, 1502, 1215 cm$^{-1}$; $^1$H NMR (CDCl$_3$): δ 6.92–8.10 (m, 13H), 4.72 (s, 2H), 4.21 (s, 2H), 3.21 (t, 2H), 2.48 (t, 2H); $^{13}$C NMR (CDCl$_3$): δ 165.5, 162.5, 160.6, 149.9, 148.5, 140.3, 137.8, 129.9, 128.7, 128.5, 128.2, 127.2, 126.7, 124.3, 123.5, 121.8, 119.1, 115.7, 115.3, 114.7, 114.2, 54.9, 48.9, 47.9, 25.5. Anal. Calcd. for C$_{25}$H$_{22}$FN$_3$ (383.46): C, 78.30; H, 5.78; N, 10.96. Found: C, 78.73; H, 5.75; N, 11.08.

Data for Compound 29 were as follows: yield 84%; mp 133–135° C.; IR (KBr): 3420, 1621, 1509, 1218 cm$^{-1}$; $^1$H NMR (CDCl$_3$): δ 6.57–8.15 (m, 12H), 4.71 (s, 2H), 4.13 (s, 2H), 3.67 (s, 6H), 3.23 (t, 2H), 2.56 (t, 2H); $^{13}$C NMR (CDCl$_3$): δ 162.1, 160.6, 149.5, 149.0, 141.4, 139.2, 1291, 128.4, 128.2, 127.2, 126.5, 123.7, 121.7, 121.5, 119.8, 106.6, 106.3, 99.6, 55.6, 55.2, 48.8, 47.9, 25.5. Anal. Calcd. for C$_{27}$H$_{27}$N$_3$O$_2$ (425.52): C, 76.21; H, 6.40; N, 9.87. Found: C, 76.23; H, 6.36; N, 9.50.

The compounds N-(1-Benzyl-2,3-dihydro-1H-pyrrolo[2,3-b]quinolin-4-yl)-acetamide (Compound 30), N-(1-Benzyl-2,3-dihydro-1H-pyrrolo[2,3-b]quinolin-4-yl)-2-piperidin-1-yl-acetamide (Compound 31), N-(1-Benzyl-2,3-dihydro-1H-pyrrolo[2,3-b]quinolin-4-yl)-2-phenyl-acetamide (Compound 32), N-(1-Benzyl-2,3-dihydro-1H-pyrrolo[2,3-b]quinolin-4-yl)-2-fluoro-6-trifluoromethyl-benzamide (Compound 33), N-(1-Benzyl-2,3-dihydro-1H-pyrrolo[2,3-b]quinolin-4-yl)-4-fluoro-3-trifluoromethyl-benzamide (Compound 34), and N-(1-Benzyl-2,3-dihydro-1H-pyrrolo[2,3-b]quinolin-4-yl)-2,3,6-trifluoro-benzamide (Compound 35) were synthesized by adding a solution of Compound 25 (1 mmol) in DMF (10 mL) dropwise to a suspension of sodium hydride (1 mmol) in DMF (20 mL) at 0° C. under nitrogen atmosphere. After 5 minutes, a corresponding acyl chloride was slowly added (over 20 minutes) to the mixture via syringe at −5° C. and the reaction mixture was stirred at room temperature for 1–4 hours (see Table II). The reaction mixture was then filtered through a pad of silical gel, the solvent was removed under reduced pressure, and the residue was purified by flash silica gel chromatography (chloroform-methanol) to yield Compounds 30–35 (see Table II).

Data for Compound 30 were as follows: yield 60%; mp 176–178° C.; IR (KBr): 3435, 2959, 1712, 1665, 1507 cm$^{-1}$; $^1$H NMR (CDCl$_3$): δ 7.27–7.73 (m, 9H), 4.76 (s, 2H), 3.47 (t, 2H), 2.98 (t, 2H), 2.29 (s, 3H); $^{13}$C NMR (CDCl$_3$): δ 169.5, 162.4, 149.2, 138.6 136.2, 129.3, 129.2, 128.7, 127.9, 126.4, 123.3, 121.9, 115.7, 115.3, 114.7, 114.2, 48.6, 48.5, 25.7, 23.8. Anal. Calcd. for C$_{20}$H$_{19}$N$_3$O (317.38): C, 75.69; H, 6.03; N, 13.24. Found: C, 75.82; H, 6.11; N, 12.94.

Data for Compound 31 were as follows: yield 49%; mp 220–222° C.; IR (KBr): 3410, 1699, 1660, 1505 cm$^{-1}$; $^1$H NMR (DMSO-d$_6$): δ 7.05–7.78 (m, 9H), 4.60 (s, 2H), 4.46 (s, 2H), 3.46 (m, 2H), 3.10 (m, 4H), 2.86 (t, 2H), 1.72 (m, 4H), 1.52 (m, 2H); $^{13}$C NMR (DMSO-d$_6$): δ 168.6, 163.6, 149.6, 145.9, 139.5, 129.9, 129.7, 129.5, 128.6, 126.6, 122.7, 121.9, 118.4, 102.4, 60.6, 54.5, 49.5, 24.1, 23.9, 22.7. Anal. Calcd. for C$_{25}$H$_{28}$N$_4$O.HCl (437.02): C, 68.70; H, 6.70; N, 12.81. Found: C, 68.81; H, 6.43; N, 12.76.

Data for Compound 32 were as follows: yield 52%; mp 157–159° C.; IR (KBr): 3431, 2959, 1690, 1665, 1507, 1310 cm$^{-1}$; $^1$H NMR (DMSO-d$_6$): δ 7.29–8.37 (m, 14H), 5.17 (s, 2H), 3.93 (s, 2H), 3.77 (t, 2H), 2.97 (t, 2H); $^{13}$C NMR (DMSO-d$_6$): δ 169.5, 156.5, 139.4, 137.2, 136.4, 135.1, 131.7, 129.9, 129.5, 129.1, 129.0, 128.8, 127.4, 125.3, 124.6, 123.6, 119.9, 118.8, 51.0, 50.5, 43.1, 25.8. Anal. Calcd. for C$_{26}$H$_{23}$N$_3$O.H$_2$O (411.50): C, 75.88; H, 6.13; N, 10.21. Found: C, 76.29; H, 6.41; N, 9.82.

Data for Compound 33 were as follows: yield 55%; mp 189–191° C.; IR (KBr): 3427, 2933, 1691, 1628, 1119 cm$^{-1}$; $^1$H NMR (DMSO-d$_6$): δ 7.35–8.25 (m, 12H), 5.02 (s, 2H), 3.66 (t, 2H), 2.98 (t, 2H); $^{13}$C NMR (DMSO-d$_6$): δ 168.5, 165.3, 164.8, 161.2, 156.4, 148.4, 138.6, 136.4, 134.5, 131.1, 129.3, 128.7, 128.3, 124.1, 123.3, 122.5, 119.4, 119.1, 118.6, 116.3, 99.7, 50.3, 49.8, 23.8. Anal. Calcd. for C$_{26}$H$_{19}$F$_4$N$_3$O (465.44): C, 67.09; H, 4.11; N, 9.03. Found: C, 67.45; H, 4.19; N, 9.15.

Data for Compound 34 were as follows: yield 45%; mp 195–197° C.; IR (KBr): 3435, 1691, 1626, 1375, 1118 cm$^{-1}$; $^1$H NMR (DMSO-d$_6$): δ 7.25–8.62 (m, 12H), 4.95 (s, 2H), 3.37 (t, 2H), 3.00 (t, 2H); $^{13}$C NMR (DMSO-d$_6$): δ 169.0, 165.0, 164.9, 161.2, 155.4, 147.9, 138.8, 136.0, 134.3, 131.0, 129.1, 128.7, 128.2, 124.1, 123.1, 122.5, 119.4, 119.1, 118.3, 116.7, 99.5, 50.8, 49.5, 23.5. Anal. Calcd. for C$_{26}$H$_{19}$F$_4$N$_3$O (465.44): C, 67.09; H, 4.11; N, 9.03. Found: C, 67.50; H, 4.05; N, 9.18.

Data for Compound 35 were as follows: yield 53%; mp 160–162° C.; IR (KBr): 3430, 1689, 1378, 1119 cm$^{-1}$; $^1$H NMR (DMSO-d$_6$): δ 7.33–8.31 (m, 11H), 5.14 (s, 2H), 3.84

(t, 2H), 3.13 (t, 2H); $^{13}C$ NMR (DMSO-$d_6$): δ 168.9, 165.3, 164.8, 161.2, 159.2, 159.1, 159.0, 138.2, 135.6, 132.3, 130.0, 129.4, 129.3, 125.9, 125.6, 124.5, 120.9, 120.5, 120.2, 119.6, 113.9, 113.4, 50.7, 49.8, 23.6. Anal. Calcd. for $C_{25}H_{18}F_3N_3O$ (433.43): C, 69.28; H, 4.19; N, 9.69. Found: C, 69.28; H, 4.07; N, 9.62.

EXAMPLE 4

Reversal of P-gp-Mediated or MRP-Mediated MDR by Pyrroloquinolines

The ability of the pyrroloquinoline compounds of the present invention to reverse P-gp-mediated or MRP-mediated MDR was analyzed as described in Example 2.

The results obtained for forty pyrroloquinoline compounds are shown in Tables III and IV. Tested pyrroloquinoline compounds were found to have an intrinsic cytotoxicity towards MCF-7 cells. Cytotoxicity is expressed as either the percent of MCF-7 cells killed by 10 μg/ml of the pyrroloquinoline compound (Table III) or the concentration of pyrroloquinoline compound required to kill 50% of the cells (Table IV). Table III illustrates the wide range of toxicity of the pyrroloquinoline compounds that were tested—the toxicity varying from 0% for Compound 62 to 99% for Compounds 36 and 50. While toxicity toward cultured cancer cells is a typical and desired property for drugs having utility in the treatment of cancer, it is desirable that chemosensitizing compounds have low intrinsic toxicity. A number of the pyrroloquinoline compounds that were examined were found to have low cytotoxicity (Tables III and IV).

The P-gp antagonism score was calculated by dividing the percent survival of NCI/ADR cells treated with the compound alone by the percent survival of NCI/ADR cells treated with the compound in the presence of 50 nM vinblastine. Chemosensitization is indicated by a score of more than 1.0. Several of the pyrroloquinoline compounds that were tested demonstrated this property (Tables III and IV).

The MRP antagonism score was calculated by dividing the percent survival of MCF-7/VP cells treated with the compound alone by the percent survival of MCF-7/VP cells treated with the compound in the presence of 1 nM vincristine. Chemosensitization is indicated by a score greater than 1.0. While some of the pyrroloquinoline compounds that were tested demonstrated this property, several pyrroloquinoline compounds were found to be effective inhibitors of P-gp without inhibiting the action of MRP (Tables III and IV). For example, Compound 62 has a P-gp antagonism score of 17.8 and a MRP antagonism score of only 1.1.

EXAMPLE 5

Anti-MDR Activity of Pyrroloquinolines

Figure 7:
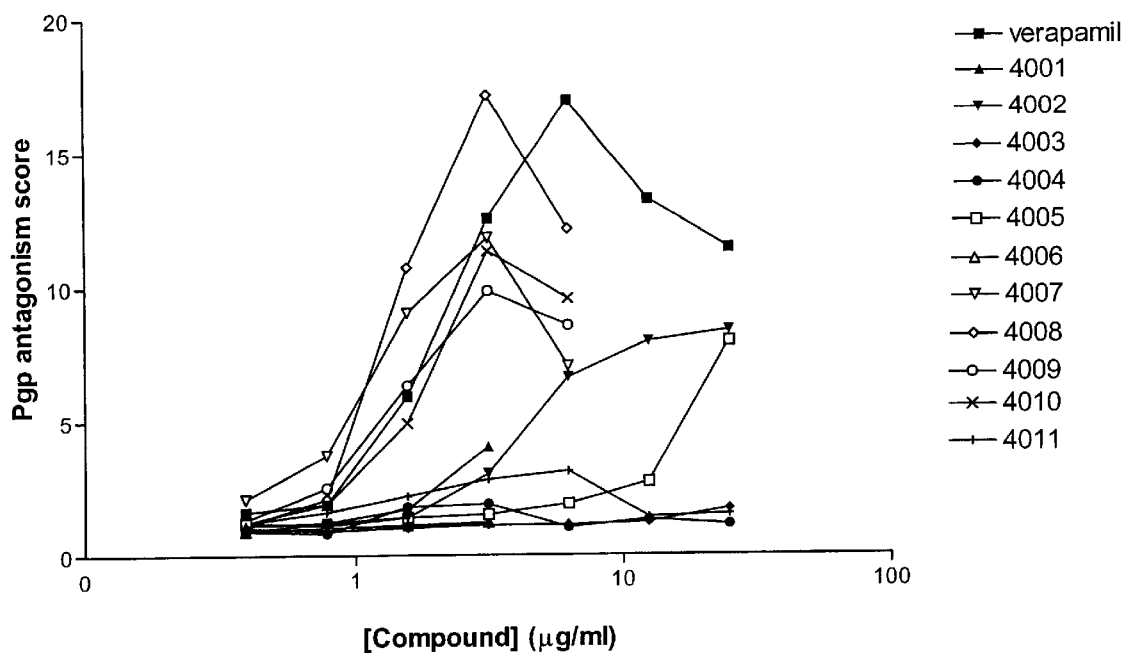
FIG. 7 illustrates the antagonism of P-gp by verapamil and pyrroloquinoline compounds.
Figure 8:
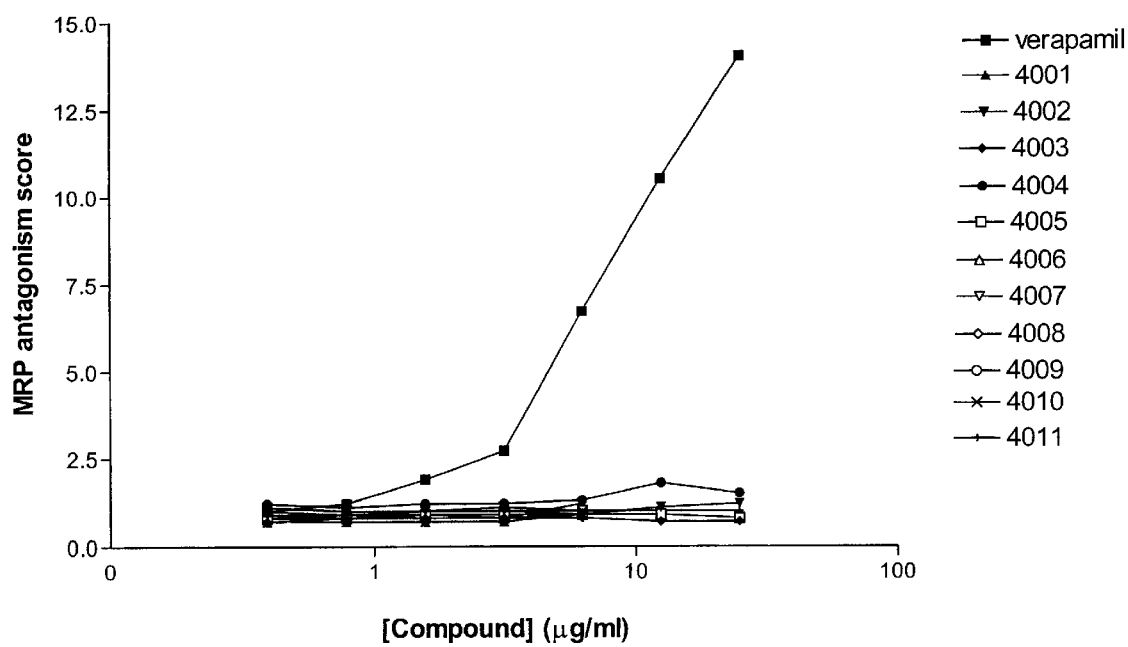
FIG. 8 illustrates the lack of antagonism of MRP1 by pyrroloquinoline compounds.

Additional pyrroloquinones were synthesized and evaluated for inhibitory activity using a panel of cell lines that exhibit the MDR phenotype due to the overexpression of either P-gp or MRP1. The abilities of these compounds to antagonize P-glycoprotein and MRP1 are shown in FIGS. 7 and 8. The P-gp antagonism score was calculated by dividing the percent survival of NCI/ADR cells treated with 50 nM vinblastine by the percent survival of NCI/ADR cells treated with the compound in the presence of 50 nM vinblastine. The MRP1 antagonism score was calculated by dividing the percent survival of MCF-7/VP cells treated with 1 nM vincristine by the percent survival of MCF-7/VP cells treated with the compound in the presence of vincristine. Larger antagonism scores indicate increasing activity and a score of 1.0 indicates no activity.

Verapamil, which is highly effective at reversing MDR in vitro, was used as a positive control in experiments examining the ability of pyrroloquinoline compounds to antagonize P-gp. Compounds 4007 and 4008 were found to be somewhat more potent than verapamil, with Compound 4008 having a maximal activity equivalent to that of verapamil (FIG. 7). However, while verapamil also effectively inhibits MRP1, none of the pyrroloquinoline compounds tested were found to affect this transporter (FIG. 8). Furthermore, neither Compound 4007 nor Compound 4008 were found to be excessively cytotoxic to the cells, thereby providing a therapeutic index of at least 10-fold. These experiments indicate that both Compounds 4007 and Compound 4008 are P-gp-selective antagonists with higher potencies than the non-selective antagonist verapamil.

The specificity of Compound 4008 is illustrated in Table V. The Reversal Index (RI) was calculated by dividing the $IC_{50}$ in the absence either verapamil or Compound 4008 by the $IC_{50}$ in the presence of 10 μM of either verapamil or Compound 4008. Both verapamil and Compound 4008 were found to enhance the cytotoxicities of Pgp-substrate drugs (including vinblastine, vincristine, and Taxol) toward cell lines that overexpress P-gp (i.e., NCI/ADR, P388/Adr and A498 cells). In contrast, neither compound strongly affected the toxicities of these drugs toward cell lines that do not overexpress P-gp (i.e., T24 and MCF-7), and neither compound affected the toxicities of non-P-gp substrate drugs (i.e., cisplatin and 5-fluorouracil) towards any of the cell lines. Therefore, the modulatory effects appear to be due to the inhibition of drug transport by P-gp. The difference in transporter selectivity between Compound 4008 and verapamil is also illustrated by the marked ability of verapamil to enhance the toxicity of vincristine toward MRP1-overexpressing MCF7/VP cells, whereas Compound 4008 has no effect on the toxicity of this drug toward MCF7/VP cells. Additional experiments also indicate that Compound 4008 increases the accumulation of [$^3$H]Taxol and [$^3$H]vinblastine by NCI/ADR cells without affecting the accumulation of these drugs by MCF-7 or MCF-7/VP cells.

It should be understood that the foregoing disclosure emphasizes certain specific embodiments of the invention and that all modifications or alternatives equivalent thereto are within the spirit and scope of the invention as set forth in the appended claims.

TABLE I

Cytotoxicity and MDR Antagonism by Phenoxymethylquinoxalinones

| Compound | $R_1$ | $R_2$ | $IC_{50}$ (μM) | P-gp | MRP1 | P-gp/MRP1 |
|---|---|---|---|---|---|---|
| 1 | H | $CH_3$ | >94 | 3.7 | 1.0 | 3.7 |
| 2 | 4-fluoro | $CH_3$ | 26 | 1.2 | 0.8 | 1.4 |
| 3 | 4-cyano | $CH_3$ | >43* | 3.2 | 0.8 | 3.9 |
| 4 | 2,3,4,5,6-pentafluoro | $CH_3$ | >70 | 2.1 | 0.8 | 2.6 |
| 5 | 4-benzyloxy | $CH_3$ | >40 | 1.9 | 0.9 | 2.2 |
| 6 | 3-tert-butyl | $CH_3$ | 19 | 4.1 | 0.9 | 4.5 |

TABLE I-continued

Cytotoxicity and MDR Antagonism by Phenoxymethylquinoxalinones

| Compound | $R_1$ | $R_2$ | $IC_{50}$ ($\mu M$) | P-gp | MRP1 | P-gp/MRP1 |
|---|---|---|---|---|---|---|
| 7 | 3,4-dichloro | $CH_3$ | >37* | 1.1 | 0.9 | 1.3 |
| 8 | 4-benzoyl | $CH_3$ | >67 | 4.7 | 0.9 | 4.9 |
| 9 | 3-methyl-4-nitro | $CH_3$ | >77 | 1.6 | 1.1 | 1.4 |
| 10 | 4-$CO_2CH_3$-2-$OCH_3$ | $CH_3$ | 71 | 5.6 | 1.1 | 5.2 |
| 11 | 2-C(O)NH-phenyl | $CH_3$ | >32* | 3.6 | 1.0 | 3.6 |
| 12 | 3-(dimethylamino) | $CH_3$ | 57 | 1.1 | 0.9 | 1.1 |
| 13 | ethyl 4-carboxylate | $CH_3$ | >74 | 3.8 | 0.9 | 4.2 |
| 14 | 3-(N-phenylamine) | $CH_3$ | 25 | 1.3 | 0.9 | 1.5 |
| 15 | 2-benzyl | $CH_3$ | 8.1 | 1.0 | 1.1 | 0.9 |
| 16 | 3-hydroxypyridine | $CH_3$ | >56 | 1.0 | 1.1 | 0.9 |
| 17 | 4-phenyl | $CH_3$ | 30 | 2.5 | 0.7 | 3.7 |
| 18 | 2-C(O)NH-phenyl | benzyl | >54 | 12.4 | 0.9 | 13.4 |
| 19 | 2-benzo | $CH_3$ | 20 | 1.0 | 0.9 | 1.2 |
| 20 | 3-benzo | $CH_3$ | 40 | 1.2 | 0.9 | 1.3 |
| 21 | 3,5-dimethoxy | $CH_3$ | 25 | 1.2 | 0.9 | 1.3 |
| 22 | 3,4-dimethoxy | $CH_3$ | 28 | 1.1 | 0.9 | 1.2 |
| 23 | 3,4,5-trimethoxy | $CH_3$ | 21 | 1.2 | 0.9 | 1.3 |

*Accurate $IC_{50}$ values could not be obtained because of low solubilities of the compounds. The values indicate the maximum doses tested.

TABLE II

Reaction Conditions, Yields, and Melting Points of Pyrroloquinolines

| Compound | Reaction Conditions | | Yield | mp |
|---|---|---|---|---|
| | Cat[a] | Time (h) | (%)[b] | (° C.) |
| 26 | A | 1.5 | 61 | 132–134 |
| 27 | A | 2 | 65 | 170–171 |
| 28 | A | 3 | 80 | 167–169 |
| 29 | A | 3 | 84 | 133–135 |
| 30 | B | 1 | 60 | 176–178 |
| 31 | B | 4 | 49 | 220–222 |
| 32 | B | 3 | 52 | 157–159 |
| 33 | B | 2 | 55 | 189–191 |
| 34 | B | 1.5 | 45 | 195–197 |
| 35 | B | 2 | 53 | 160–162 |

[a]A: potassium tert-butoxide; B: sodium hydride.
[b]Isolated yield.

TABLE III

Cytotoxicity and MDR Antagonism by Pyrroloquinolines

| Compound | $R_1$ | $R_2$ | $R_3$ | Toxicity | Pgp Antagonism | MRP Antagonism |
|---|---|---|---|---|---|---|
| 36 | methyl | H | 7-Br | 94 | 1.3 | 1.6 |
| 37 | methyl | | | 12 | 1.6 | 1.0 |
| 38 | methyl | | | 22 | 5.6 | 1.0 |
| 39 | methyl | | | 39 | 1.8 | 1.4 |

TABLE III-continued

Cytotoxicity and MDR Antagonism by Pyrroloquinolines

| Compound | R₁ | R₂ | R₃ | Toxicity | Pgp Antagonism | MRP Antagonism |
|---|---|---|---|---|---|---|
| 40 | methyl | *[structure: –C(=O)CH₂NH-tBu]* | | 28 | 3.2 | 1.2 |
| 41 | methyl | *[structure: –C(=O)CH₂N(Et)₂]* | | 30 | 6.0 | 1.2 |
| 42 | methyl | *[structure: –C(=O)CH₂-piperidine]* | | 51 | 4.1 | 1.2 |
| 43 | methyl | *[structure: –C(=O)CH₂N(nBu)₂]* | | 50 | 4.2 | 1.3 |
| 44 | methyl | *[structure: –C(=O)CH₂NH-CH₂CH₂-C₆H₄-OH]* | | 21 | 1.7 | 1.4 |
| 45 | methyl | *[structure: –C(=O)-adamantyl]* | | 29 | 4.7 | 0.9 |
| 46 | methyl | *[structure: –C(=O)CH₂CH₂-(3,5-di-tBu-4-OH-C₆H₂)]* | | 99 | 1.0 | 1.0 |
| 47 | methyl | *[structure: –C(=CH₂... )(Ph)(piperidinyl)]* | | 58 | 2.4 | 1.0 |
| 48 | butyl | H | 7-Br | 98 | 1.1 | 1.0 |
| 49 | cyclohexyl | H | | 97 | 0.8 | 0.6 |
| 50 | cyclohexyl | H | 7-Br | 99 | 1.0 | 1.0 |

TABLE III-continued
Cytotoxicity and MDR Antagonism by Pyrroloquinolines
| Compound | R₁ | R₂ | R₃ | Toxicity | Pgp Antagonism | MRP Antagonism |
|---|---|---|---|---|---|---|
| 51 | phenyl | H | | 52 | 2.7 | 1.1 |
| 52 | 3-chloro-benzyl | 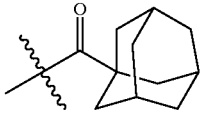 | | 33 | 1.2 | 1.2 |
| 53 | benzyl | H | | 47 | 3.1 | 1.0 |
| 54 | benzyl | H | 7-Br | 94 | 1.7 | 1.3 |
| 55 | benzyl | H | 7-CH₃ | 98 | 0.7 | 1.0 |
| 56 | benzyl | H | 9-CH₃ | 77 | 1.6 | 1.7 |
| 57 | benzyl | H | 6,9-CH₃ | 81 | 1.5 | 1.2 |
| 58 | benzyl | H | 7,9-CH₃ | 49 | 3.6 | 1.4 |
| 59 | benzyl | 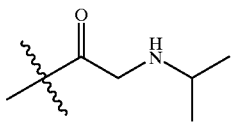 | | 45 | 13.0 | 0.99 |
| 60 | benzyl | 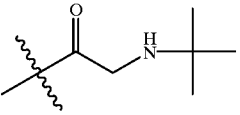 | | 29 | | |
| 61 | benzyl | 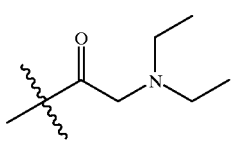 | | 14 | 14.8 | 0.98 |
| 62 | benzyl | 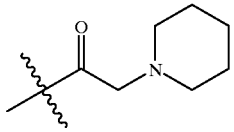 | | 0 | 17.8 | 1.09 |
| 63 | benzyl | 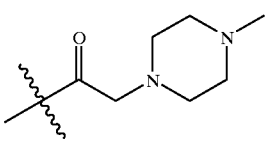 | | 21 | 7.5 | 1.07 |
| 64 | benzyl | 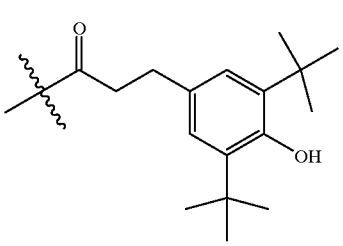 | | 50 | 13.2 | 1.15 |

TABLE IV

Cytotoxicity and MDR Antagonism by Pyrroloquinolines

| Compound | $R_1$ | $R_2$ | Toxicity $IC_{50}$ (μg/ml) | Antagonism at $IC_{20}$ or less P-gp | MRP | Maximum Antagonism (conc. μg/ml) |
|---|---|---|---|---|---|---|
| 4001 | benzyl | H | 1.7 | 1.0 | 1.0 | 4.0(3.1) |
| 4002 | benzyl | ethyl propanoate | 12 | 0.9 | 0.9 | 8.3(25) |
| 4003 | benzyl | 3-fluorobenzyl | >25 | 1.2 | 0.7 | 1.7(25) |
| 4004 | benzyl | 4-fluorobenzyl | >25 | 1.3 | 0.7 | 1.3(12.5) |
| 4005 | benzyl | 3,5-dimethoxybenzyl | 20 | 1.4 | 0.9 | 7.9(25) |
| 4006 | benzyl | 2,3,6-trifluorophenacyl | 3.5 | 1.1 | 0.9 | 2.3(12.5) |
| 4007 | benzyl | piperidinyl acetone | 6 | 9.0 | 1.0 | 11.8(3.1) |
| 4008 | benzyl | phenacyl | 5 | 10.7 | 0.7 | 17.1(3.1) |
| 4009 | benzyl | 2-trifluoromethyl-6-fluorophenacyl | 6 | 2.5 | 0.9 | 9.8(3.1) |

TABLE IV-continued

Cytotoxicity and MDR Antagonism by Pyrroloquinolines

| Compound | R₁ | R₂ | Toxicity IC$_{50}$(μg/ml) | Antagonism at IC$_{20}$ or less P-gp | MRP | Maximum Antagonism (conc. μg/ml) |
|---|---|---|---|---|---|---|
| 4010 | benzyl | 3-trifluoromethyl-4-fluorobenzoyl | 9 | 4.9 | 0.9 | 11.3(3.1) |
| 4011 | benzyl | 2,3,6-trifluorobenzoyl | >25 | 3.1 | 1.0 | 3.1(6.25) |

TABLE V

Cell Line-Specificity and Drug-Specificity of the Effects of Compound 4008 and Verapamil

| Cell Line | Drug | EtOH IC$_{50}$ | Verapamil IC$_{50}$ | RI | 4008 IC$_{50}$ | RI |
|---|---|---|---|---|---|---|
| | | Non-Pgp Cell Lines | | | | |
| T24 | Vinblastine (nM) | 1.3 ± 0.3 | 0.5 ± 0.1 | 2.7 | 0.4 ± 0.1 | 3.8 |
| | Taxol (nM) | 4.7 ± 0.5 | 3.0 ± 0.4 | 1.6 | 4.0 ± 0.6 | 1.2 |
| | Vincristine (nM) | 4.8 ± 0.2 | 1.3 ± 0.2 | 3.7 | 2.2 ± 0.6 | 1.5 |
| | Cisplatin (μM) | 6.7 ± 1.1 | 7.0 ± 0.8 | 1.0 | 5.8 ± 1.2 | 1.1 |
| | 5-Fluorouracil (μM) | 77 ± 20 | 48 ± 6 | 1.6 | 29 ± 8 | 2.6 |
| MCF-7 | Vinblastine (nM) | 0.4 ± 0.1 | 0.3 ± 0.1 | 1.2 | 0.2 ± 0 | 1.8 |
| | Taxol (nM) | 1.6 ± 0.3 | 1.4 ± 0.6 | 1.1 | 1.8 ± 0.1 | 0.9 |
| | Vincristine (nM) | 0.6 ± 0.1 | 0.1 ± 0.1 | 4.6 | 0.4 ± 0.1 | 0.9 |
| | Cisplatin (μM) | 16 ± 5 | 14 ± 4 | 1.1 | 19 ± 5 | 0.8 |
| | 5-Fluorouracil (μM) | 49 ± 31 | 53 ± 20 | 0.9 | 30 ± 15 | 1.6 |
| MCF7/VP (MRP1) | Vinblastine (nM) | 0.6 ± 0.1 | 0.2 ± 0 | 2.4 | 0.4 ± 0.1 | 1.3 |
| | Taxol (nM) | 1.8 ± 0.4 | 1.6 ± 0.4 | 1.1 | 2.1 ± 0.4 | 0.8 |
| | Vincristine (μM) | 7.5 ± 1.1 | 0.5 ± 0.2 | 15.0 | 7.3 ± 0.9 | 1.0 |
| | Cisplatin (μM) | 8.5 ± 2.1 | 10.5 ± 3.2 | 0.8 | 11.3 ± 0.5 | 0.8 |
| | 5-Fluorouracil (μM) | 11 ± 1 | 12 ± 2 | 0.9 | 16 ± 3 | 0.7 |
| | | Pgp Cell Lines | | | | |
| NCI/ADR | Vinblastine (nM) | 110 ± 17 | 0.6 ± 0.1 | 173 | 3.1 ± 2.0 | 35 |
| | Taxol (nM) | 2020 ± 810 | 19 ± 5 | 106 | 29 ± 5 | 70 |
| | Vincristine (nM) | 183 ± 14 | 3.7 ± 0.8 | 50 | 10.5 ± 1.1 | 18 |
| | Cisplatin (μM) | 7.0 ± 0.9 | 6.3 ± 0.8 | 1.1 | 6.0 ± 0.5 | 1.2 |
| | 5-Fluorouracil (μM) | 181 ± 84 | 210 ± 99 | 0.9 | 175 ± 74 | 1.0 |
| P388/ADR | Vinblastine (nM) | 28 ± 5 | 0.5 ± 0.1 | 61 | 0.5 ± 0.1 | 63 |
| | Taxol (nM) | 1650 ± 470 | 5.0 ± 1.4 | 330 | 8.2 ± 2.9 | 202 |
| | Doxorubicin (μM) | 26.7 ± 10.6 | 0.03 ± 0.01 | 1000 | 0.13 ± 0.09 | 200 |
| | Vincristine (nM) | 150 ± 24 | 1.3 ± 0.5 | 112 | 5.0 ± 2.9 | 30 |
| | Cisplatin (μM) | 2.1 ± 0.8 | 1.1 ± 0.3 | 2.0 | 1.1 ± 0.4 | 1.9 |
| | 5-Fluorouracil (μM) | 0.22 ± 0.04 | 0.30 ± 0.08 | 0.7 | 0.32 ± 0.08 | 0.7 |
| A498 | Vinblastine (nM) | 7.6 ± 2.6 | 0.9 ± 0.5 | 8.5 | 0.43 ± 0.12 | 18 |
| | Taxol (nM) | 49 ± 21 | 2.7 ± 0.5 | 18 | 7.3 ± 3.4 | 6.8 |
| | Vincristine (nM) | 62 ± 11 | 1.3 ± 0.3 | 49 | 3.5 ± 1.1 | 18 |
| | Cisplatin (μM) | 4.6 ± 1.0 | 5.4 ± 0.9 | 0.8 | 6.0 ± 1.4 | 0.8 |
| | 5-Fluorouracil (μM) | 9.0 ± 2.1 | 8.0 ± 2.8 | 1.1 | 13.0 ± 5.0 | 0.7 |

What we claim is:

1. A compound of the formula:

[Structure: quinoxalin-2-one with R2 on N1, R3 on benzo ring, and 3-position substituted with -(CH2)n-O-phenyl-R1]

or a pharmaceutically acceptable salt thereof, wherein n is an integer from 1 to 6;

$R_1$ is H, alkyl ($C_1$–$C_{15}$), cycloalkyl, cycloalkylalkyl, aryl, arylalkyl, halogen, haloalkyl, —OH, alkoxy, hydroxyalkyl, alkanoyl, —CONH$_2$, —CONH($C_1$–$C_6$ alkyl), —CON($C_1$–$C_6$ alkyl)($C_1$–$C_6$ alkyl), —CF$_3$, —OCF$_3$, —NH$_2$, —CO$_2$R$_8$, —OC(O)R$_8$, mono- or dialkylamino, aminoalkyl, or mono- or dialkylaminoalkyl;

$R_3$ is H, alkyl ($C_1$–$C_{15}$), cycloalkyl, cycloalkylalkyl, aryl, arylalkyl, halogen, haloalkyl, —OH, alkoxy, hydroxyalkyl, alkanoyl, —CONH$_2$, —CONH($C_1$–$C_6$ alkyl), —CON($C_1$–$C_6$ alkyl)($C_1$–$C_6$ alkyl), —CF$_3$, —OCF$_3$, —NO$_2$, —NH$_2$, —CO$_2$R$_8$, —OC(O)R$_8$, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, or —NR'R", wherein R' and R" are independently H or alkyl ($C_1$–$C_6$);

$R_2$ is H, alkyl ($C_1$–$C_8$), cycloalkyl, cycloalkylalkyl, aryl, arylalkyl, halogen, haloalkyl, —OH, alkoxy, hydroxyalkyl, alkanoyl, —CONH$_2$, —CONH($C_1$–$C_6$ alkyl), —CON($C_1$–$C_6$ alkyl)($C_1$–$C_6$ alkyl), —CO$_2$R$_8$, —OC(O)R$_8$, —OC(O)NH$_2$, —OC(O)NH($C_1$–$C_6$ alkyl), —OC(O)N($C_1$–$C_6$ alkyl) ($C_1$–$C_6$ alkyl), mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, or —NR'R", wherein R' and R" are independently H or alkyl ($C_1$–$C_6$); and $R_8$ is alkyl, aryl, arylalkyl, cycloalkyl, or cycloalkylalkyl;

wherein each of the above is optionally substituted with up to 5 groups that are independently alkyl ($C_1$–$C_6$), alkoxy ($C_1$–$C_6$), halogen, —CF$_3$, —OCF$_3$, —OH, hydroxyalkyl, —CN, —CO$_2$H, or —NR'R", wherein R' and R" are independently H or alkyl ($C_1$–$C_6$).

2. A compound according to claim 1, wherein n is 1;

$R_1$ is H, alkyl ($C_1$–$C_{15}$), cycloalkyl, cycloalkylalkyl, phenyl, benzyl, halogen, haloalkyl, —OH, alkoxy, hydroxyalkyl, alkanoyl, —CONH$_2$, —CONH ($C_1$–$C_6$alkyl), —CON($C_1$–$C_6$alkyl)($C_1$–$C_6$alkyl), —CF$_3$, —OCF$_3$, —NH$_2$, —CO$_2$R$_8$, —OC(O)R$_8$, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, or —NR'R", wherein R' and R" are independently H or alkyl ($C_1$–$C_6$);

$R_2$ is H, alkyl ($C_1$–$C_8$), cycloalkyl, cycloalkylalkyl, phenyl, benzyl, halogen, haloalkyl, —OH, alkoxy, hydroxyalkyl, alkanoyl, —CONH$_2$, —CONH ($C_1$–$C_6$alkyl), —CON($C_1$–$C_6$alkyl)($C_1$–$C_6$alkyl), —CO$_2$R$_8$, —OC(O)R$_8$, carbamoyl, mono or dialkylcarbamoyl, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, —CN, or —NR'R", wherein R' and R" are independently H or alkyl ($C_1$–$C_6$);

$R_3$ is H, alkyl ($C_1$–$C_6$), alkoxy, halogen, alkanoyl, —CF$_3$, or —OCF$_3$; and $R_8$ is alkyl, aryl, arylalkyl, cycloalkyl, or cycloalkylalkyl;

wherein each of the above is optionally substituted with up to 5 groups that are independently alkyl ($C_1$–$C_6$), alkoxy ($C_1$–$C_6$), halogen, —CF$_3$, —OCF$_3$, —OH, hydroxyalkyl, —CN, —CO$_2$H, or —NR'R", wherein R' and R" are independently H or alkyl ($C_1$–$C_6$).

3. A chemical compound according to claim 1 that is 1-Methyl-3-phenoxymethyl-1H-quinoxalin-2-one; 3-(4-Cyano-phenoxymethyl)-1-methyl-1H-quinoxalin-2-one; 3-(3-tert-Butyl-phenoxymethyl)-1-methyl-1H-quinoxalin-2-one; 3-(4-Benzoyl-phenoxymethyl)-1-methyl-1H-quinoxalin-2-one; 4-(4-Methyl-3-oxo-3,4-dihydro-quinoxalin-2-ylmethoxy)-benzoyl ethyl ester; or pharmaceutically acceptable salts thereof.

4. A pharmaceutical composition comprising a compound of the formula:

[Structure: same quinoxalin-2-one scaffold]

or a pharmaceutically acceptable salt thereof, with at least one pharmaceutically acceptable carrier or excipient wherein n is an integer from 1 to 6;

$R_1$ is H, alkyl ($C_1$–$C_{15}$), cycloalkyl, cycloalkylalkyl, aryl, arylalkyl, halogen, haloalkyl, —OH, alkoxy, hydroxyalkyl, alkanoyl, —CONH$_2$, —CONH($C_1$–$C_6$ alkyl), —CON($C_1$–$C_6$ alkyl)($C_1$–$C_6$ alkyl), —CF$_3$, —OCF$_3$, —NH$_2$, —CO$_2$R$_8$, —OC(O)R$_8$, mono- or dialkylamino, aminoalkyl, or mono- or dialkylaminoalkyl;

$R_3$ is H, alkyl ($C_1$–$C_{15}$), cycloalkyl, cycloalkylalkyl, aryl, arylalkyl, halogen, haloalkyl, —OH, alkoxy, hydroxyalkyl, alkanoyl, —CONH$_2$, —CONH($C_1$–$C_6$ alkyl), —CON($C_1$–$C_6$ alkyl)($C_1$–$C_6$ alkyl), —CF$_3$, —OCF$_3$, —NO$_2$, —NH$_2$, —CO$_2$R$_8$, —OC(O)R$_8$, mono- or dialkylamino, aminoalkyl, or mono- or dialkylaminoalkyl;

wherein each of the above is optionally substituted with up to 5 groups that are independently alkyl ($C_1$–$C_6$), halogen, haloalkyl, —CF$_3$, —OCF$_3$, —OH, alkoxy, hydroxyalkyl, or —NR'R", wherein R' and R" are independently H or alkyl ($C_1$–$C_6$);

$R_2$ is H, alkyl ($C_1$–$C_8$), cycloalkyl, cycloalkylalkyl, aryl, arylalkyl, halogen, haloalkyl, —OH, alkoxy, hydroxyalkyl, alkanoyl, —CONH$_2$, —CONH(C$_1$–C$_6$ alkyl), —CON(C$_1$–C$_6$ alkyl)(C$_1$–C$_6$ alkyl), —CO$_2$R$_8$, —OC(O)R$_8$, —OC(O)NH$_2$, —OC(O)NH(C$_1$–C$_6$ alkyl), —OC(O)N(C$_1$–C$_6$ alkyl) (C$_1$–C$_6$ alkyl), mono- or dialkylamino, aminoalkyl, or mono- or dialkylaminoalkyl;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, or —NR'R", wherein R' and R" are independently H or alkyl (C$_1$–C$_6$); and R$_8$ is alkyl, aryl, arylalkyl, cycloalkyl, or cycloalkylalkyl; wherein each of the above is optionally substituted with up to 5 groups that are independently alkyl (C$_1$–C$_6$), alkoxy (C$_1$–C$_6$), halogen, —CF$_3$, —OCF$_3$, —OH, hydroxyalkyl, —CN, —CO$_2$H, or —NR'R", wherein R' and R" are independently H or alkyl (C$_1$–C$_6$).

5. A pharmaceutical composition according to claim 4, wherein n is 1;

R$_1$ is H, alkyl (C$_1$–C$_{15}$), cycloalkyl, cycloalkylalkyl, phenyl, benzyl, halogen, haloalkyl, —OH, alkoxy, hydroxyalkyl, alkanoyl, —CONH$_2$, —CONH(C$_1$–C$_6$alkyl), —CON(C$_1$–C$_6$alkyl)(C$_1$–C$_6$alkyl), —CF$_3$, —OCF$_3$, NH$_2$, —CO$_2$R$_8$, —OC(O)R$_8$, mono- or dialkylamino, aminoalkyl, or mono- or dialkylaminoalkyl;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, or —NR'R", wherein R' and R" are independently H or alkyl (C$_1$–C$_6$);

R$_2$ is H, alkyl (C$_1$–C$_8$), cycloalkyl, cycloalkylalkyl, phenyl, benzyl, halogen, haloalkyl, —OH, alkoxy, hydroxyalkyl, alkanoyl, —CONH$_2$, —CONH(C$_1$–C$_6$alkyl), -CON(C$_1$–C$_6$alkyl)(C$_1$–C$_6$alkyl), —CO$_2$R$_8$, —OC(O)R$_8$, carbamoyl, mono or dialkylcarbamoyl, mono- or dialkylamino, aminoalkyl, or mono- or dialkylaminoalkyl;

wherein each of the above is optionally substituted with up to 5 groups that are independently alkyl (C$_1$–C$_6$), halogen, haloalkyl, —CF$_3$, —OCF$_3$, —OH, alkoxy, hydroxyalkyl, —CN, or —NR'R", wherein R' and R" are independently H or alkyl (C$_1$–C$_6$);

R$_3$ is H, alkyl (C$_1$–C$_6$), alkoxy, halogen, alkanoyl, —CF$_3$, or —OCF$_3$; and R$_8$ is alkyl, aryl, arylalkyl, cycloalkyl, or cycloalkylalkyl; wherein each of the above is optionally substituted with up to 5 groups that are independently alkyl (C$_1$–C$_6$), alkoxy (C$_1$–C$_6$), halogen, —CF$_3$, —OCF$_3$, —OH, hydroxyalkyl, —CN, —CO$_2$H, or —NR'R", wherein R' and R" are independently H or alkyl (C$_1$–C$_6$).

6. A pharmaceutical composition according to claim 4 comprising a compound that is 1-Methyl-3-phenoxymethyl-1H-quinoxalin-2-one; 3-(4-Cyano-phenoxymethyl)-1-methyl-1H-quinoxalin-2-one; 3-(3-tert-Butyl-phenoxymethyl)-1-methyl-1H-quinoxalin-2-one; 3-(4-Benzoyl-phenoxymethyl)-1-methyl-1H-quinoxalin-2-one; or Methyl-3-oxo-3,4-dihydro-quinoxalin-2-ylmethoxy)-benzoyl ethyl ester; or pharmaceutically acceptable salts thereof; with at least one pharmaceutically acceptable carrier or excipient.

7. The pharmaceutical composition of either claim 4, 5, or 6 further comprising at least one additional chemotherapeutic agent.

8. A compound that is 3-methoxy-4-(4-methyl-3-oxo-3,4-dihydroquinoxalin-2-yl-methoxy)-benzoyl methyl ester; 2-(4-methyl-3-oxo-3,4-dihydroquinoxalin-2-yl-methoxy)-N-phenylbenzamide; or 2-(4-benzyl-3-oxo-3,4-dihydroquinoxalin-2-ylmethoxy)-N-phenylbenzamide; or pharmaceutically acceptable salts thereof.

9. A pharmaceutical composition comprising a compound that is 3-methoxy-4-(4-methyl-3-oxo-3,4-dihydroquinoxalin-2-yl-methoxy)-benzoyl methyl ester; 2-(4-methyl-3-oxo-3,4-dihydroquinoxalin-2-yl-methoxy)-N-phenylbenzamide; or 2-(4-benzyl-3-oxo-3,4-dihydroquinoxalin-2-ylmethoxy)-N-phenylbenzamide; or pharmaceutically acceptable salts thereof and at least one pharmaceutically acceptable carrier or excipient.

10. A method for inhibiting drug transport from target cells or tissues in an animal undergoing chemotherapy, comprising administering to the animal the pharmaceutical composition of claim 4, 5, or 6 in an amount effective to inhibit drug transport.

11. The method of claim 10, wherein drug transport is mediated by P-glycoprotein.

12. A method for preventing drug resistance in target cells or tissues in an animal undergoing chemotherapy, comprising administering to the animal the pharmaceutical composition of claim 4, 5, or 6 in an amount effective to attenuate drug resistance in the target cells or tissues of the animal.

13. A method for enhancing the therapeutic efficacy of an antiproliferative drug in target cells or tissues of an animal undergoing chemotherapy, comprising administering to the animal the pharmaceutical composition of claim 4, 5, or 6 in an amount effective to enhance delivery of the antiproliferative drug to the target cells or tissues of the animal.

* * * * *